(12) United States Patent
Torrent et al.

(10) Patent No.: US 6,489,142 B1
(45) Date of Patent: Dec. 3, 2002

(54) METHODS AND COMPOSITIONS FOR PRODUCING VIRAL PARTICLES

(75) Inventors: Christophe Torrent, Paris (FR);
Patrice Yeh, Gif sur Yvette (FR);
Michel Perricaudet, Ecrosnes (FR);
David Klatzmann, Paris (FR);
Jean-Loup Salzmann, Paris (FR)

(73) Assignees: Aventis Pharma S.A., Antony (FR);
Genopoietic, Paris (FR)

( * ) Notice: Subject to any disclaimer, the term of this patent is extended or adjusted under 35 U.S.C. 154(b) by 0 days.

(21) Appl. No.: 09/700,422

(22) PCT Filed: May 18, 1999

(86) PCT No.: PCT/FR99/01184

§ 371 (c)(1),
(2), (4) Date: Jan. 25, 2001

(87) PCT Pub. No.: WO99/60144

PCT Pub. Date: Nov. 25, 1999

(30) Foreign Application Priority Data

May 18, 1998 (FR) .............................. 98 06258

(51) Int. Cl.[7] .......................... C12P 21/06; C12P 21/04; C12P 21/08; C12Q 1/68; C07H 21/04
(52) U.S. Cl. .......................... 435/69.1; 435/6; 435/69.7; 530/387.3; 536/23.4; 536/23.72
(58) Field of Search .......................... 435/6, 69.1, 69.7; 530/387.3; 536/23.4, 23.72

(56) References Cited

FOREIGN PATENT DOCUMENTS

| WO | 97 32481 | 9/1997 |
|---|---|---|
| WO | 98 22143 | 5/1998 |

OTHER PUBLICATIONS

Bilbao G. et al.: "Adenoviral/retroviral vector chimeras: a novel strategy to achieve high–efficiency stable transduction in vivo." FASEB Journal, vol. 11, (1997), pp. 624–634.

Miller N. et al.: "Targeted Vectors for Gene Therapy" FASEB Journal, vol. 9, No. 2, (Feb. 1995) pp. 190–199.

Dedieu J.–F. et al.: "Long–term gene delivery into the livers of immunocompetent mice with E1/E4–defective adenovirus." Journal of Virology, vol. 71, No. 6, (Jun. 1997) pp. 4626–4637.

Gao et al, "Biology of Adenovirus Vectors with E1 and E4 Deletions for Liver Directed Gene Therapy", Journal of Virology; Dec. 1996, vol. 70, No. 12, pp. 8934–8943.

Brough et al, "Activation of Transgene Expression by Early Region 4 is Responsible for a High Level of Persistent Transgene Expression from Adenovirus Vectors in Vivo", Journal of Virology, Dec. 1997, vol. 71, No. 12, pp. 9206–9213.

*Primary Examiner*—Hankyel T. Park
(74) *Attorney, Agent, or Firm*—Nixon & Vanderhye P.C.

(57) ABSTRACT

The invention concerns methods and constructs for producing retroviral particles, in vitro, ex vivo or in vivo. It also concerns the use of said methods and constructs for transferring nucleic acids into cells. More particularly, the invention concerns a composition comprising the whole set of genetic elements required for constituting a retroviral particle, incorporated in one or several recombinant adenoviruses defective for all or part of the regions E1 and E4 at least (adenoviral/retroviral chimeric vectors).

26 Claims, 15 Drawing Sheets

METHODS AND COMPOSITIONS FOR PRODUCING VIRAL PARTICLES

Figure 1:
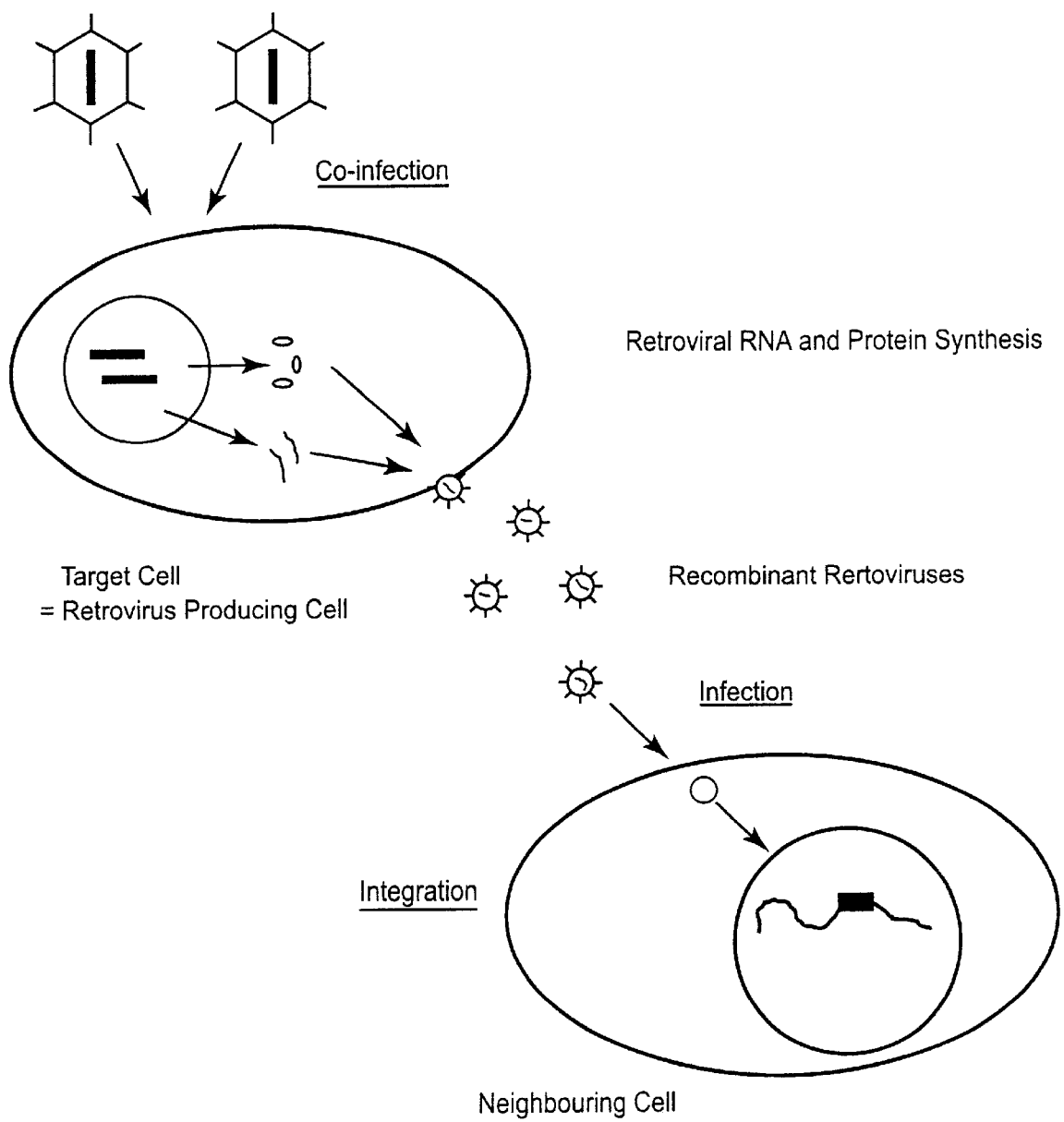

The present invention relates to the field of biotechnology. More particularly, it concerns methods and constructs for producing retroviral particles in vitro, ex vivo or in vivo. It also concerns the use of such methods and constructs for transferring nucleic acids into cells.

Retroviruses are currently one of the main types of vector for transferring nucleic acids into cells. They are used for example for transferring nucleic acids in vitro or ex vivo (experimental studies, study of regulation, production of recombinant proteins, introduction of resistance genes or toxicity genes) or directly in vivo (establishment of animal pathological models, labeling or bioavaiiability studies, therapeutic use by grafting producer cells or injecting purified virus, etc.).

For all these utilizations, it is therefore important to have effective methods available for producing and administering retroviruses. In this respect, conventional methods are based on the use of packaging cell lines. Such cell lines are constructed in vitro and express the whole set of proteins required for constituting and packaging a defective retroviral vector in a retroviral particle. Such cell lines are exemplified by the cell lines PSICRIP [Danos and Mulligan, PNAS (1988) 85: 6460], PA317 [Miller and Buttimore, Mol. Cell. Biol. (1986) 6: 2895], or GP+ Env AM12 [Markowitz et al., Virology (1988) 167: 400]. However, the use of such cell lines can pose certain problems, related first to their construction and second, to their use.

For example, such cell lines must be stable, that is, express the retroviral functions in a continuous manner, without genetic rearrangements or loss of expression. In addition, such cell lines must be compatible with the potential pharmacological use of the retroviruses, and must therefore be established from cells that can be cultured, having little or no immunogenicity, etc.

Furthermore, it is important that the cell lines used produce fairly high viral titers free of replication-competent virus (RCV). The methods of retroviral preparation by means of packaging cell lines therefore necessarily comprise quality controls on both the viral stocks produced and the cell lines used. Finally, depending on the desired application, these production methods may have to be carried out under a high level of confinement, further complicating the industrial scalability of such methods.

To address these drawbacks, patent application WO 95/22617 proposed a new concept for producing retroviral particles that avoids the use of retrovirus packaging cells. This new concept consists in transforming a target cell in vitro, ex vivo or directly in vivo to a retrovirus producing cell, by introducing into this cell the whole set of genetic elements required for constituting a retroviral particle. This application provides in particular for transferring these elements by means of plasmid constructs or viral vectors of different origin. As a matter of fact, Feng et al. [Nature Biotechnology (1997) 15: 866] have described a specific embodiment of this new approach, using two first generation recombinant adenoviruses (i.e. defective for the E1 region) into which the retroviral genetic elements have been distributed in a precise arrangement.

The present application now describes a further improvement to the retroviral particle production methods described hereinabove, and the use for transferring nucleic acids.

The present application is based in particular on the use of recombinant adenoviruses for delivering to cells, in vitro, ex vivo or in vivo, the whole set of genetic elements required for constituting a retroviral particle. As compared to previously described works, the present application is based in part on the use of specific types of recombinant adenovirus and/or on a specific distribution of the retroviral genetic elements. As demonstrated in the present application, the methods and constructs according to the invention make it possible to obtain high levels of retroviral particle production, are effective, and display increased safety in vitro, ex vivo as well as in vivo. Furthermore, the defective recombinant retroviruses so produced are infectious, and are capable of transferring a nucleic acid into a cell with high efficiency.

A first subject of the invention therefore concerns a composition comprising the whole set of genetic elements required for constituting a retroviral particle, incorporated in one or several recombinant adenoviruses defective for all or part of the E1 and E4 regions at least.

In the context of the invention, the term "genetic elements required for constituting a retroviral particle" refers to the whole set of nucleic acid sequences, coding and regulatory, which in cis or in trans are necessary and sufficient to constitute a retroviral particle, that is, a physical particle expressing the retroviral envelope at its surface, and inside of which are found the different proteins required to carry out a retroviral replication cycle, and a genome in a form which allows it to be reverse transcribed.

The organization of the retroviral genome is well understood, and comprises primarily the following elements:

An LTR region located at each end of the retroviral genome, serving in particular as origin of transcription and transcriptional promoter. This LTR region more specifically contains elements designated U3, R and U5 (see FIG. 5, for example). The U5 sequence, together with the U3 sequence, plays a key role during provirus integration.

A packaging sequence (Psi or ψ), involved in packaging the retroviral genome in the viral particle. The packaging sequence may further contain a region extending to certain elements of the gag gene, which have been reported to improve packaging efficiency.

Three coding regions, named gag, pol and env, coding for the core proteins (gag), enzymes (reverse transcriptase, protease, integrase), and the retroviral envelope (env), respectively.

To constitute a recombinant retroviral particle, a retroviral vector is generally constructed comprising genetic elements acting in cis, i.e., the LTR regions and the packaging sequence, and in which all or part of the gag, pol and/or env coding regions (acting in trans) have been deleted. Normally, such a retroviral vector also comprises a nucleic acid of interest (transgene). The coding regions not present or inactive in the retroviral vector are provided in trans (complementation functions) so as to be able to reconstitute a retroviral particle.

In a specific embodiment of the invention, the genetic elements therefore comprise a retroviral vector and nucleic acids coding for retroviral complementation functions (that is, for functions defective in the retroviral vector, eg., gag, pol and/or env).

In a more particular embodiment of the present invention, the genetic elements comprise:
- a nucleic acid coding for a retroviral gag protein,
- a nucleic acid coding for a retroviral pol protein,
- a nucleic acid coding for an envelope protein, for example a retroviral env protein, and
- a nucleic acid comprising, between two LTR regions, a retroviral packaging sequence and a nucleic acid sequence of interest.

To carry out the present invention, the genetic elements may be derived from different types of retrovirus, such as ecotropic and/or amphotropic viruses. In particular, these may be retroviruses belonging to the family of oncoviruses, lentiviruses or spumaviruses. In the oncovirus family, particular examples include the slow oncoviruses, which do not carry an oncogene, such as for example MoMLV, ALV, BLV or MMTV, and rapid oncoviruses, such as RSV for example. In the lentivirus family, examples include HIV, SIV, FIV or CAEV.

Furthermore, the LTR region or regions used may either be complete retroviral LTR regions, or subdomains allowing reconstitution of complete LTR regions after reverse transcription. Thus, the LTR regions used may comprise deletions of domains such as U3 and U5 for example. In a specific embodiment of the invention, the retroviral vector comprises a 5' LTR deleted for the U3 region and a 3' LTR deleted for the U5 region. The use of this type of construct allows in particular to stabilize the vector during the construction steps and to lower the risks of recombination. The genetic elements may be directly prepared from isolated retroviruses, according to methods known to those skilled in the art, and/or synthesized artificially. Such elements may be amplified in culture, as described in the examples. Moreover, the nucleic acids used may be DNA or RNA.

In a preferred variant, the genetic elements are such that they code for the retroviral gag and pol proteins and for an envelope protein allowing infection of human cells. More preferably still, the gag and pol proteins are proteins from retroviruses chosen from among MoMLV, ALV, BLV, MMTV or RSV, and the envelope protein is a protein from viruses chosen from A4070, GALV, RD114, VSV-G or rabies virus. It is understood that the invention may also be carried out by using variants or mutants of these proteins, having conserved their biological activity, or chimeric or hybrid proteins allowing to modify the tropism of the retroviral particle, especially by giving it specificity for certain cell types.

In a particular embodiment, the envelope protein is therefore a viral or cellular protein, allowing the retroviral particles to infect human cells. It is preferably a protein from a virus such as A4070, GALV, RD114, VSV-G or rabies virus. The preferred viral envelopes are A4070, GALV or VSV-G. The preferred gag and pol proteins come from the MoMLV retrovirus.

According to a specific embodiment of the invention, the genetic elements allow constitution of a lentivirus particle, and therefore derive, at least in part, from a lentivirus, such as HIV, SIV, FIV or CAEV in particular. The use of recombinant retroviruses prepared from lentiviruses has been described in the literature and offers certain advantages for transferring genes into quiescent cells [Poeschia et al., Nature Medicine (1998) 4: 354]. The present invention now makes it possible to exploit this property to achieve, under improved conditions, gene transfer by lentiviruses.

The disposition of the retroviral genetic elements in the adenovirus or adenoviruses may be accomplished in several ways.

Thus, in one variant embodiment, the invention concerns a composition comprising the whole set of genetic elements required for constituting a retroviral particle distributed into three separate recombinant adenoviruses.

In this particular embodiment, a composition according to the invention comprises for example a first recombinant adenovirus comprising, incorporated in its genome, the nucleic acid or acids encoding gag and pol; a second adenovirus comprising, incorporated in its genome, a nucleic acid encoding the envelope protein; and a third recombinant adenovirus comprising, incorporated in its genome, the retroviral vector.

In another, preferred variant embodiment, the invention concerns a composition comprising the whole set of genetic elements required for constituting a retroviral particle distributed into two separate recombinant adenoviruses. In this respect, an especially preferred composition in the context of the invention comprises:

a first recombinant adenovirus comprising, incorporated in its genome, one or several nucleic acids coding for the retroviral proteins gag and pol, and
 a second recombinant adenovirus comprising, incorporated in its genome, a nucleic acid coding for an envelope protein such as defined hereinabove, and a nucleic acid comprising, between two complete LTR regions or subdomains allowing reconstitution of complete LTRs following reverse transcription, a retroviral packaging sequence and a nucleic acid sequence of interest.

The use of such a composition is illustrated in a general way in FIG. 1. As shown in the examples, this specific distribution of retroviral genetic elements makes it possible to obtain high titers of infectious retroviral particles, capable of efficiently and stably transferring a transgene into the cells of interest.

In this respect, a specific subject of the present application concerns any defective recombinant adenovirus, characterized in that it comprises, incorporated in its genome, one or several nucleic acids coding for the retroviral proteins gag and pol, and
 any defective recombinant adenovirus, characterized in that it comprises, incorporated in its genome, a nucleic acid coding for an envelope protein, and a nucleic acid comprising, between two LTR regions complete or not, a retroviral packaging sequence and a nucleic acid sequence of interest.

In particular, such adenoviruses may be defective for all or part of the E1 (E1A and/or E1B), E2, and/or E4 region, for example.

A further specific subject of the invention concerns a composition comprising two adenoviruses such as set forth hereinabove.

Another, equally preferred variant embodiment of the invention concerns a composition comprising the whole set of genetic elements required for constituting a retroviral particle, incorporated in a single recombinant adenovirus.

The special advantage of this embodiment is based notably on its simplified implementation due to the use of a single adenovirus.

It is understood that the compositions according to the invention can be adapted by those skilled in the art according to the structure of the retroviral vector, and particularly the defective retroviral genes therein. Thus, the vector used may be defective for one, two or all the retroviral genes gag, pol and env. Depending on the case, the composition and distribution of adenoviruses in the compositions of the invention may be readily adapted. However, a preferred embodiment is that in which the retroviral vector is defective for the whole set of genes gag, pol and env, as illustrated in the examples, and that adapted to producing recombinant lentiviruses.

In the compositions of the invention, the nucleic acid used coding for a retroviral protein gag, pol or env generally comprises a transcriptional promoter located 5' of the coding region, and a transcriptional terminator located 3' of the coding region. The promoters used may vary in their nature, origin and properties. The choice of promoter depends in fact on the desired use and on the transgene, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, EF1-α, APO, CMV, etc. or artificial promoters, such as those for p53. E2F or cAMP.

Preferably, the promoter controlling the expression of gag, pol and env is a strong constitutive promoter. Moreover, the promoter may also comprise an "enhancer" region to increase the efficiency of expression. The choice of the terminator region may also be effortlessly made by those skilled in the art, particularly among the terminators of the genes GH, SV40, EF1-α, etc., widely described in the literature. Finally, the nucleic acids coding for gag and pol are often used in the form of a bicistronic unit, controlled by a single promoter and terminator, as is the case in the retroviral genome.

As noted hereinabove, the advantages of the present invention derive notably from the distribution of the retroviral genetic elements in the adenoviruses, and/or from the type of adenovirus used. In this respect, as underscored above, the adenoviruses used in the context of the present invention are primarily defective for all or part of the E1 region and the E4 region at least. As illustrated in the examples, together with an advantageous distribution of retroviral genetic elements, this organization of the adenoviral genome procures high safety and efficiency. Furthermore, the genomic structure of the recombinant adenoviruses used also allows the production of original and advantageous distributions of the retroviral genetic elements, such as notably the use of a single adenovirus or of a combination of two adenoviruses as illustrated hereinabove. The results show, in an especially advantageous manner, that the use of this type of adenovirus and/or of specific distributions of retroviral genetic elements according to the invention makes it possible to obtain high titers of infectious retroviral particles and long-term stability of the transgene (beyond 3 months). These entirely advantageous results are surprising in so far as the absence of the viral E4 region has been described as having a negative effect on the expression of sequences introduced into an adenoviral vector. Furthermore, the results presented show that, in vivo, the compositions according to the invention induce at least a 10- to 50-fold increase in the number of transduced tumor cells, as compared to administration of an adenovirus alone. These results thus confirm the advantageous and surprising properties of the present invention for transferring nucleic acids into cells.

The adenoviruses used to carry out the present invention are therefore advantageously defective for all or part of the E1 and E4 regions at least.

Advantageously these are so-called third generation defective recombinant adenoviruses, i.e. defective for all or part of the E1 and E4 regions, and possibly for the E3 region.

Specific variants of the invention comprise the use of adenoviruses harboring deletions affecting all or a functional part of the following regions:
E1, E4 and E3,
E1, E4 and E2,
E1, E4, E2 and E3,
the regions hereinabove as well as all or part of the genes encoding the adenovirus late functions (L1 to L5), or further still,
all the viral coding regions.

The genomic structure of adenoviruses has been largely described in the literature. In this respect, the genome of adenovirus Ad5 has been fully sequenced and is accessible from data bases (see notably GeneBank M73260). Likewise, parts or even all of other adenovirus genomes (Ad2, Ad7, Ad12, canine to adenovirus CAV-2, etc.) have also been sequenced. Furthermore, the construction of defective recombinant adenoviruses has also been described in the literature. Thus, applications WO 94/28152, WO 95/02697 and WO 96/22378, for example, describe different deletions in the E1 and E4 regions. Similarly, application WO 96/10088 describes vectors bearing a modification in the Iva2 gene, application WO 94/26914 describes animal adenoviruses, and application WO 95/29993 describes deletions in the adenoviral E2 region.

Advantageously, the recombinant adenovirus used in the context of the invention comprises a deletion in the E1 region of its genome affecting the E1a and E1b regions. A specific example is provided by deletions affecting nucleotides 454–3328, 382–3446 or 357–4020 (with reference to the Ad5 genome).

Furthermore, the deletion in the E4 region preferentially affects all the open reading frames, such as for example deletions 33466–35535 or 33093–35535, or only part of the E4 region (ORF6 or ORF3 for example), as described in applications WO95/02697 and WO96/22378, incorporated herein as reference.

As for adenoviruses further deleted for late functions ("minimum" vector) or for all coding regions ("gutless" vector), their construction has been described for instance by Parks et al., PNAS (1996) 93: 13565 and Lieber et al., J. Virol. (1996) 70: 8944.

The retroviral genetic elements may be inserted at different sites in the recombinant adenoviral genome. They may be inserted in the E1, E3 or E4 region, by replacing the deleted sequences or in addition. They may also be inserted at any other site, apart from sequences required in cis for virus production (ITR sequences and packaging sequence).

Moreover, the recombinant adenoviruses may be of human or animal origin. As far as adenoviruses of human origin are concerned, those in group C may preferentially be cited, in particular the adenoviruses type 2 (Ad2), type 5 (Ad5); or adenoviruses type 7 (Ad7) or 12 (Ad12). Adenoviruses of animal origin are preferentially exemplified by the canine adenoviruses, and particularly all the strains of adenovirus CAV2 [Manhattan strain or A26/61 (ATCC VR-800), for example]. Other adenoviruses of animal origin are given notably in application WO94126914, incorporated herein as reference.

The recombinant adenoviruses are produced in packaging cells, i.e. a cell line that can complement in trans one or several of the deficient functions in the recombinant adenoviral genome. Among the packaging cells familiar to those skilled in the art, an example is cell line 293 in which part of the adenovirus genome has been integrated. More specifically, cell line 293 is a human embryonic kidney cell line containing the left extremity (approximately 11–12%) of the genome of adenovirus serotype 5 (Ad5), containing the left ITR, the packaging region, the E1 region, including E1a and E1b, the region encoding the pIX protein and part of the region encoding the plVa2 protein. This cell line is able to trans-complement recombinant adenoviruses defective for the E1 region, i.e. deleted of all or part of the E1 region, and produce viral stocks at high titers. This cell line can also produce, at permissive temperature (32° C.), stocks of virus further comprising the temperature-sensitive E2 mutation. Other cell lines capable of complementing the E1 region have been described, based notably on human lung carcinoma cells A549 (WO94/28152) or on human retinoblasts [Hum.

Gen. Ther. (1996) 215]. Moreover, cell lines capable of trans-complementing several adenoviral functions have also been described. Specific examples comprise the cell lines complementing the E1 and E4 regions [Yeh et al., J. Virol. (1996) 70: 559–565; Cancer Gen. Ther. (1995) 2: 322; Krougliak et al., Hum. Gen. Ther. (1995) 6: 15751 and cell lines complementing the E1 and E2 regions (WO94/28152, WO95/02697, WO95/27071) or cell lines derived therefrom that can be used for producing minimum adenoviruses, especially since they also express site-specific recombinase activity involved in the construction of such viruses.

The recombinant adenoviruses are normally produced by introducing viral DNA into the packaging cells, followed by cell lysis after about 2 or 3 days (the adenoviral replication cycle being 24 to 36 hours). To carry out the method, the introduced viral DNA may be the complete recombinant viral genome, possibly constructed in bacteria (WO96/25506) or yeast (WO95/03400), transfected into the cells. It may also be a recombinant virus used to infect the packaging cells. The viral DNA may also be introduced in the form of fragments each bearing a part of the recombinant viral genome and a region of homology which, after introduction into the packaging cell, allows reconstitution of the recombinant viral genome by means of homologous recombination between the different fragments.

Following cell lysis, the recombinant viral particles can be isolated by any known method such as cesium chloride gradient centrifugation or chromatography. An alternative method was notably described in application FR 9608164, incorporated herein as reference.

The compositions according to the invention may comprise variable amounts of recombinant adenovirus, easily adaptable by those skilled in the art according to the desired application (in vitro, ex vivo or in vivo, for instance).

Generally, the compositions comprise approximately $10^5$ to $10^{15}$ v.p. of each recombinant adenovirus, preferably $10^7$ to $10^{12}$ v.p.

The term v.p. corresponds to the number of viral particles present in the compositions.

Furthermore, the compositions of the invention may also be in different forms, such as solutions, gels, powder, etc. They are generally solutions, preferably sterile, such as for instance saline solutions (monosodium phosphate, disodium phosphate, sodium, potassium, calcium or magnesium chloride, etc., or mixtures of these salts), isotonic, or dry compositions, particularly lyophilizates which, by addition of sterile water or ohysiological serum, as the case may be, form reconstituted solutions. Other excipients may be used such as for example a hydrogel. Such a hydrogel may be prepared from any biocompatible, non-cytotoxic (homo or hetero) polymer. Such polymers are described in application WO93/08845 for example.

In addition, the compositions of the invention may be packaged in any suitable type of device, such as a bottle, tube, ampoule, bag, syringe, balloon, etc. Further, in compositions of the invention comprising at least two types of recombinant adenovirus, the latter may be packaged either as a mixture or individually.

As indicated hereinabove, the compositions of the invention may be used in vitro, ex vivo or in vivo.

For in vitro or ex vivo use, the cells may simply be incubated, in any suitable device (plate, dish, bag, etc.) in the presence of a composition such as described hereinabove.

As shown in FIG. 1 for a composition comprising two types of recombinant adenovirus, incubation of the cells causes the cells to be infected by the two adenoviruses, after which the coinfected cell can produce infectious retroviral particles. For this type of application, the compositions may be used at multiplicities of infection (MOI) of between 10 and 5000 v.p. per cell, for instance, preferably between 100 and 2000, as shown in particular in the examples.

In this respect, the invention equally concerns a method for producing retroviral particles in vitro comprising incubating cells in the presence of a composition such as described hereinabove, possibly followed by recovery and/or purification of the retroviruses produced. The cells that can be used in this method may be any type of cell permissive to adenovirus. These may be primary cultures or cell lines, particularly mammalian, and particularly of human origin. The use of cells of human origin (embryonic kidney cells, A549, retinoblasts, HeLa, KB, etc.) is especially advantageous because it gives the retroviral particles heightened resistance to the complement system. As shown in the examples, the method of the invention makes it possible to obtain high retroviral titers, without the use of packaging cell lines.

For it vivo use, the compositions of the invention may be formulated in is view of administration by the topical, oral, parenteral, intranasal, intravenous, intramuscular, subcutaneous, intraocular, transdermal, intratumoral, etc. route.

In this respect, the invention further concerns a method for transferring a nucleic acid in vivo comprising administering a composition such as described hereinabove. The invention may be used for instance in animals, to establish pathological models, or for the study of gene regulation, and also in humans, in labeling or bioavailability studies, or for medical purposes. The invention is also directed to the use of the compositions described hereinabove for producting infectious retroviral particles in vivo.

According to the nucleic acid of interest (transgene) inserted in the retroviral vector, the present invention may be used in a large number of applications. Thus, among the products of interest in the context of the present invention, more specific examples include enzymes, blood products, hormones such as growth hormone, cytokines, lymphokines:intedeukins, interferons, TNF, etc. (French patent 92 03120), growth factors, for example angiogenic factors such as VEGF or FGF, neurotransmitters or their precursors or synthesis enzymes, trophic factors, particularly neurotrophic factors for the treatment of neurodegenerative diseases or nervous system trauma, or macular degeneration :BDNF, CNTF, NGF, IGF, GMF aFGF, NT3, NT5, HARP/pleiotrophin, or bone growth factors, hematopoietic factors, etc., dystrophin or minidystrophin (French patent 91 11947), genes encoding coagulation factors:factors VII, VIII, IX, suicide genes (thymidine kinase, cytosine deaminase), proteins involved in the cell cycle such as p21, or other kinasedependent inhibitor proteins, Rb, Gas-1, Gas-6, Gas-3, Gad 45, Gad 153, cyclins A, B, D, or further still the GAX protein inhibiting smooth muscle cell proliferation (treatment of restenosis), apoptosis-inducing proteins or other tumor suppressors such as p53, Bax, BcIX-s, Bad or any other antagonist of Bcl2 and BcIX-1, genes for hemoglobin or other transport proteins, genes for proteins involved in lipid metabolism, of the apolipoprotein type chosen from among apolipoproteins A-I, A-II, A-IV, B, C-I, C-II, C-II, D, E, F, G, H, J and apo(a), metabolic enzymes such as for instance lipoprotein lipase, hepatic lipase, cholesterol lecithin acyltransferase, 7-alpha-cholesterol hydroxylase, phosphatidyl acid phosphatase, or still lipid transport proteins such as cholesterol ester transport protein and phospholipids transport protein, HDL binding protein or further still a receptor chosen from the LDL receptors, chylomicron-remnant receptors and scavenger receptors, etc.

Among the products of interest it is important to point out antibodies, antibody single chain variable fragments (ScFv) or any other antibody fragment with recognition capabilities for its use in immunotherapy, for example in the treatment of infectious diseases, tumors (anti-RAS, anti-p53 or anti-GAP antibodies), autoimmune diseases such as multiple sclerosis (anti-idiotype antibody).

Non-limiting examples of other proteins of interest are the soluble receptors, such as for instance the soluble CD4 receptor or the soluble TNF receptor for anti-HIV therapy, the soluble acetylcholine receptor for the treatment of myasthenia gravis; peptides which are enzyme inhibitors or substrates, or peptides which agonize or antagonize receptors or adhesion proteins such as for instance for the treatment of asthma, thrombosis and restenosis:synthetic, chimeric or truncated proteins. Among the hormones of primary interest one may cite insulin in the case of diabetes, growth hormone and calcitonin.

The nucleic acid may also be a gene or an antisense sequence, whose expression in the target cell enables control of gene expression or transcription of cellular mRNA. Such sequences may, for instance, be transcribed in the target cell to RNA complementary to cellular mRNA, thereby lo blocking its translation to protein, according to the method described in European patent 140 308. Therapeutic genes equally comprise sequences coding for ribozymes, able to selectively destroy target RNAs (European patent 321 201).

The nucleic acid may also comprise one or several genes coding for an antigenic peptide, that can elicit an immune response in humans or animals. In this particular embodiment, the invention therefore allows the production either of vaccines, or of immunotherapy treatments for use in humans or animals, notably against microorganisms, viruses or cancers. In particular these may be antigenic peptides specific of Epstein Barr virus, HIV virus, hepatitis B virus (European patent 185 573), pseudo-rabies virus, "syncitia forming virus", other viruses or yet tumor-specific antigens such as MAGE proteins (European patent 259 212).

The nucleic acid may also code for a product toxic to cells. particularly a conditional toxicity (eg., thymidine kinase, cytosine deaminase, etc.).

Other genes of interest have notably been described by Mc Kusick, V. A. Mendelian [Inheritance in man, catalogs of autosomal dominant, autosomal recessive, and X-linked phenotypes, Eighth edition. John Hopkins University Press (1988)], and by Standbury, J. B. et al. [The metabolic basis of inherited disease, Fifth edition. McGraw-Hill (1983)]. The genes of interest comprise the proteins involved in the metabolism of amino acids, lipids and other components of the cell.

Finally, the nucleic acid may comprise several coding regions, possibly separated by an IRES, allowing the production of several products of interest.

Furthermore, the transgene generally comprises a transcriptional promoter (located 5') and a transcriptional terminator (located 3'), which may be chosen by those skilled in the art, as described hereinabove. In addition, the transgene may be present in the retroviral vector in the same or the opposite orientation to the direction of LTR transcription. Finally, in a particular embodiment, the adenoviral genomes of the invention may also be delivered to cells in the form of plasmids, together with adenoviral complementation functions.

Other advantages and applications of the present invention will become more apparent from the following examples, which are given for purposes of illustration and not by way of limitation.

FIGURE LEGENDS

TABLE 1: RT activity determination in W162 cells infected or co-infected with AdTK/ENV and/or AdGAG/POL at the indicated MOI. RT activity was determined on cell supematants 2 days post-infection, as described in example 5.2. RT activity in GP+envAM12 cells served as control. The results represent the mean of at least two independent experiments (standard deviation less than 10%).

FIG. 1: General outline of the use of a composition according to the invention comprising two retroviral/adenoviral chimeric vectors=adetrovirus.

Figure 2A:
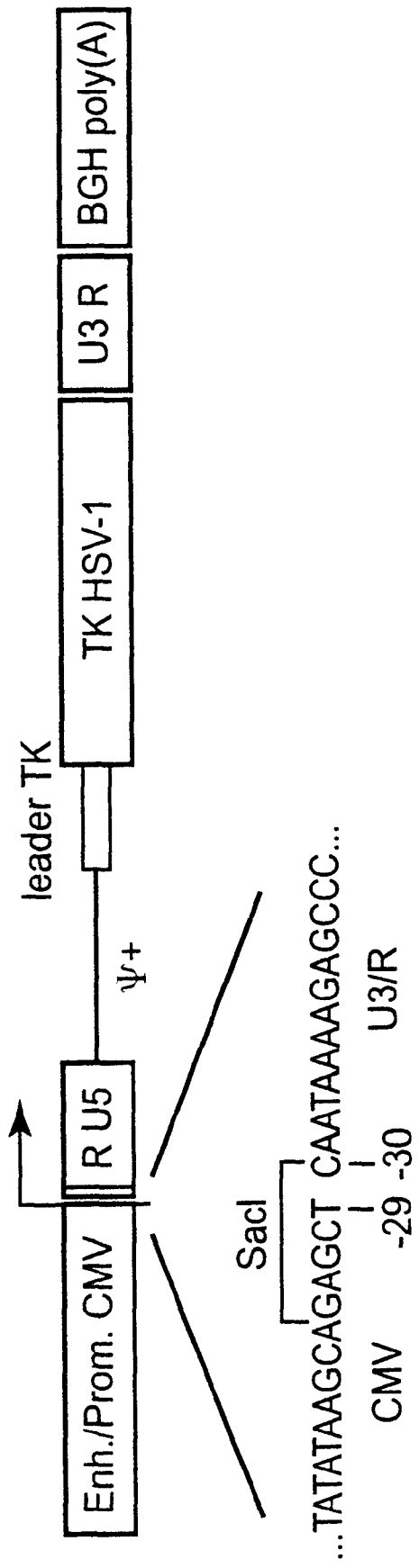

FIG. 2: Expression cassettes for retroviral complementation functions (2B, 2C) and the retroviral vector (2A).

Figure 3:
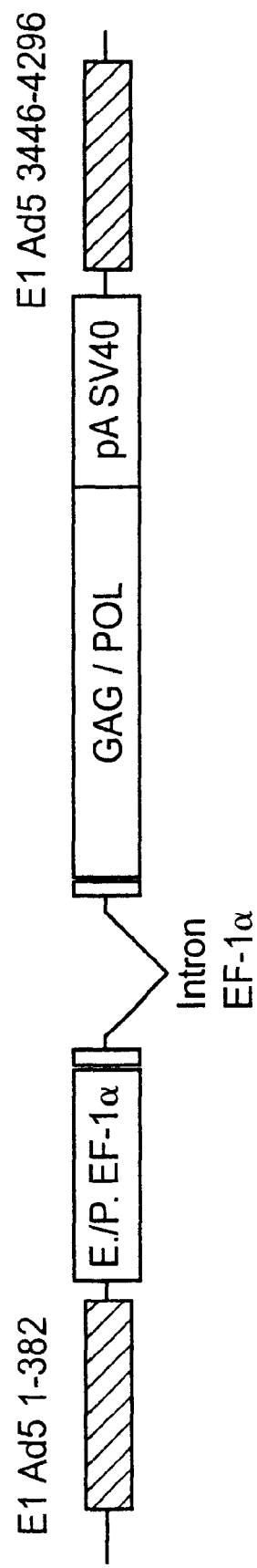

FIG. 3: Shuttle plasmid pAdEGP. E./P.-EF-1α enhancer/promoter of EF-1α gene; pA:polyadenylation site.

Figure 4:
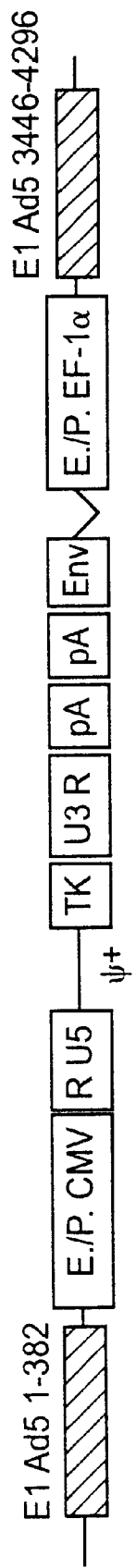

FIG. 4: Shuttle plasmid pAd CLTKEE. E./P.-CMV: CMV enhancer/promoter; pA:polyadenylation site.

Figure 5:
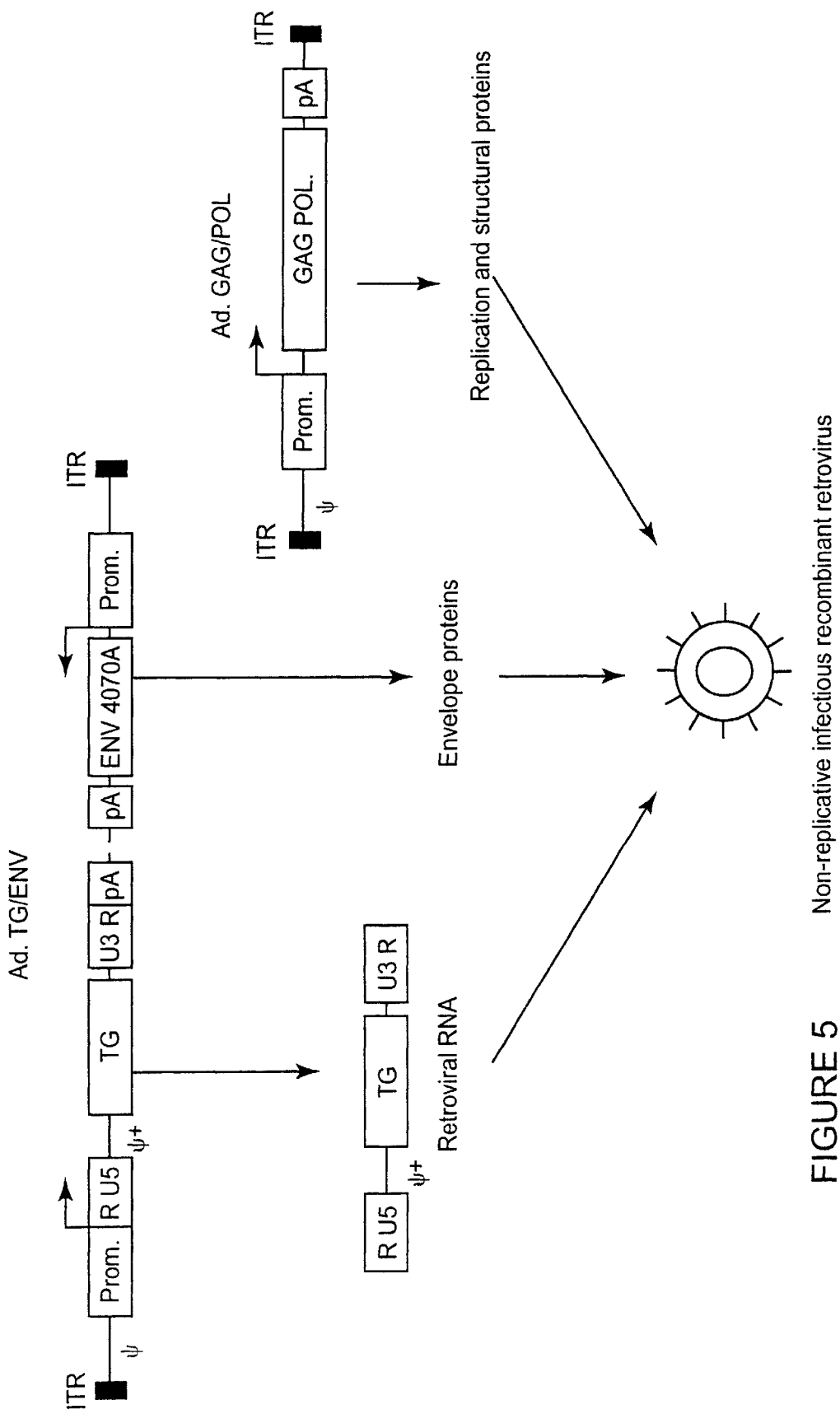

FIG. 5: Mechanism of production of infectious retroviral particles by means of a composition of the invention.

Figure 6:
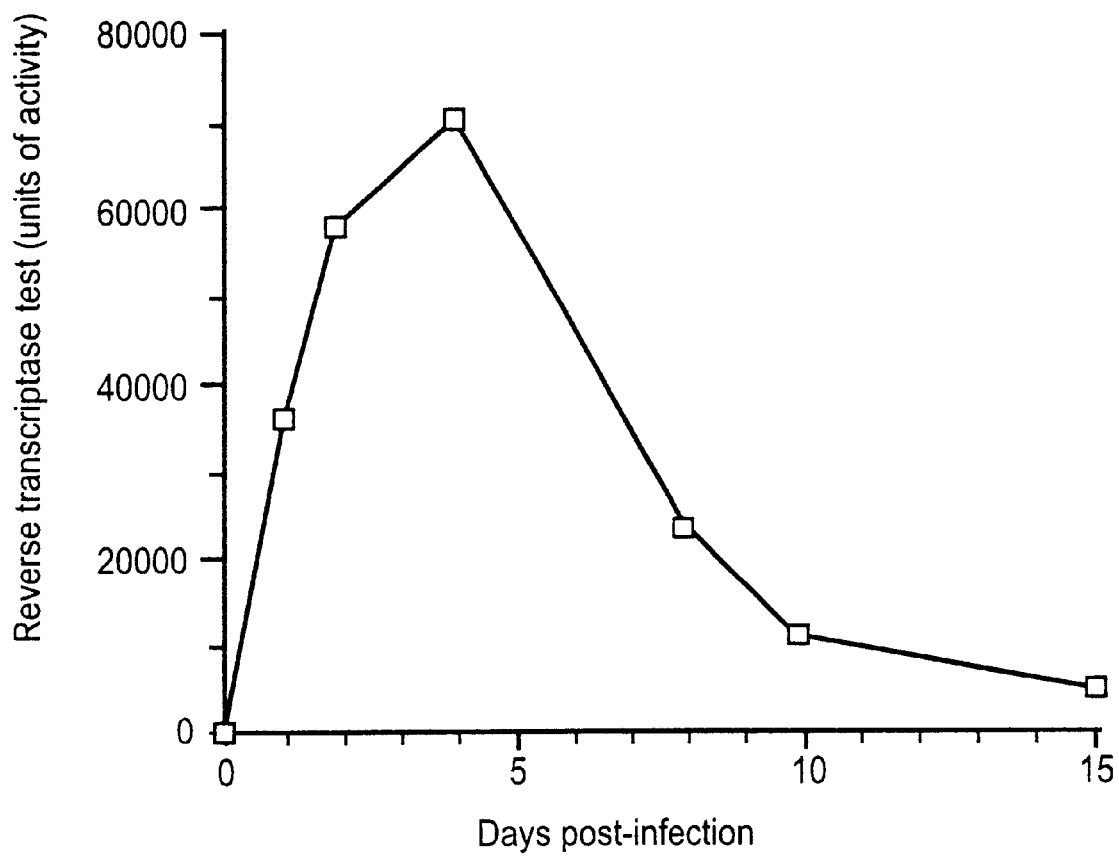

FIG. 6: Time course of retroviral particle production after co-infection of W162 cells with Ad TK/ENV and Ad GAG/POL.

Figure 7:
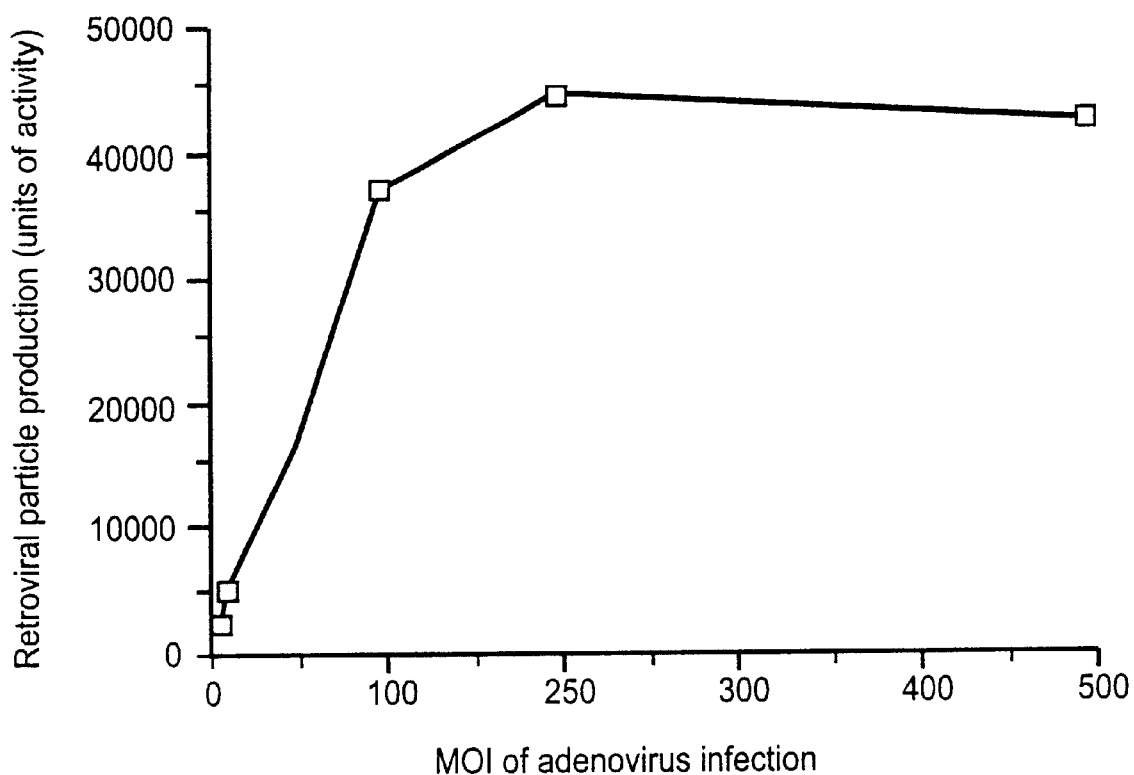

FIG. 7: Retroviral particle production in W162 cells according to MOI of adenoviral infection.

Figure 8:
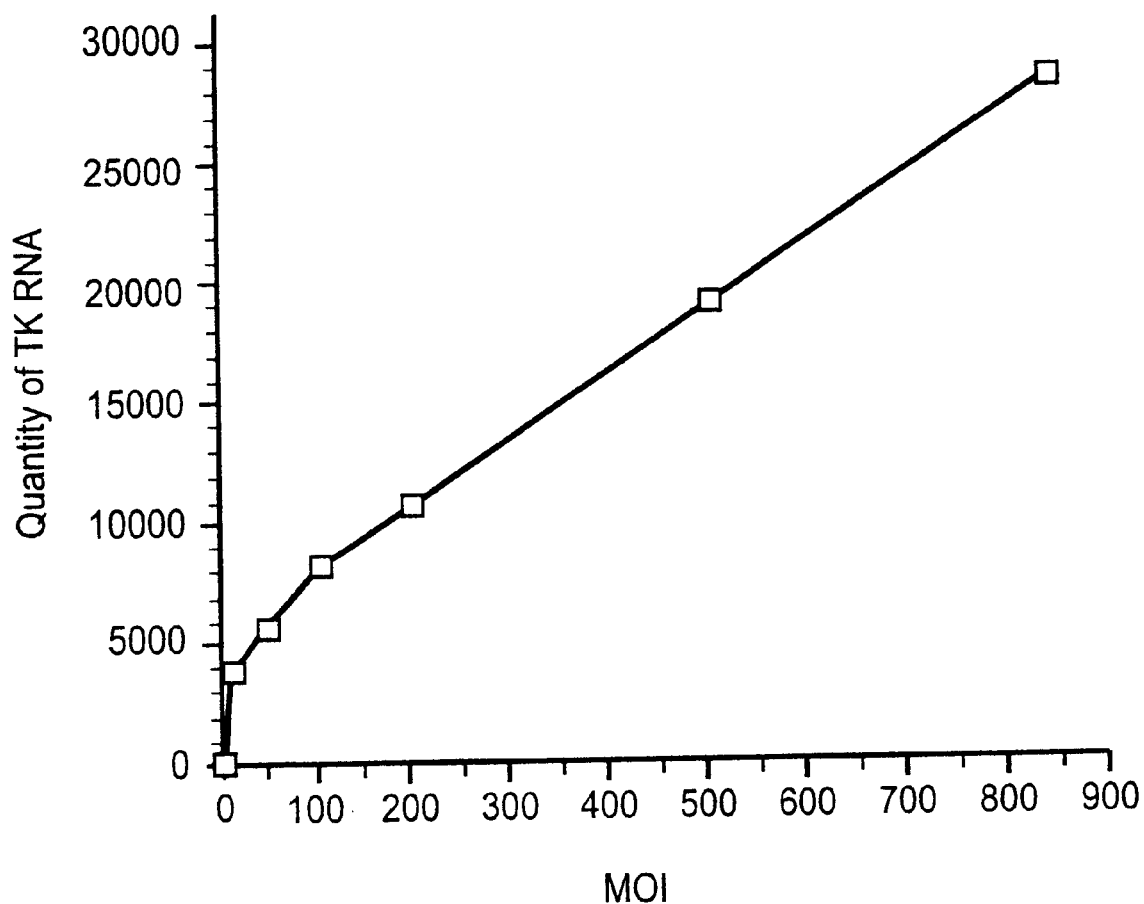

FIG. 8: Slot-blot quantification of TK+ RNA packaged in viral particles.

Figure 9:
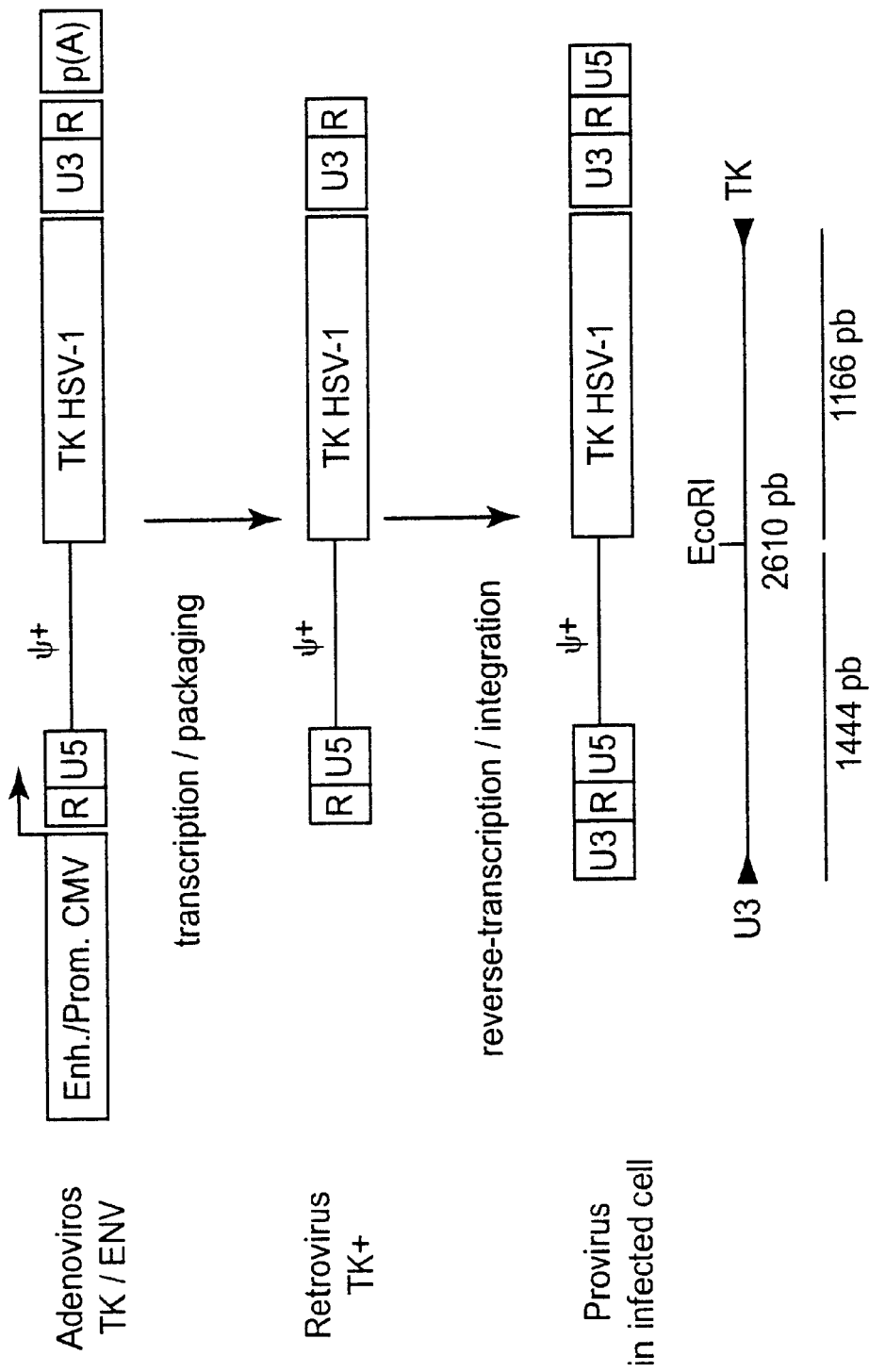

FIG. 9: Method of detection, by PCR and enzymatic cleavage, of the presence of an integrated retroviral TK expression cassette.

Figure 10:
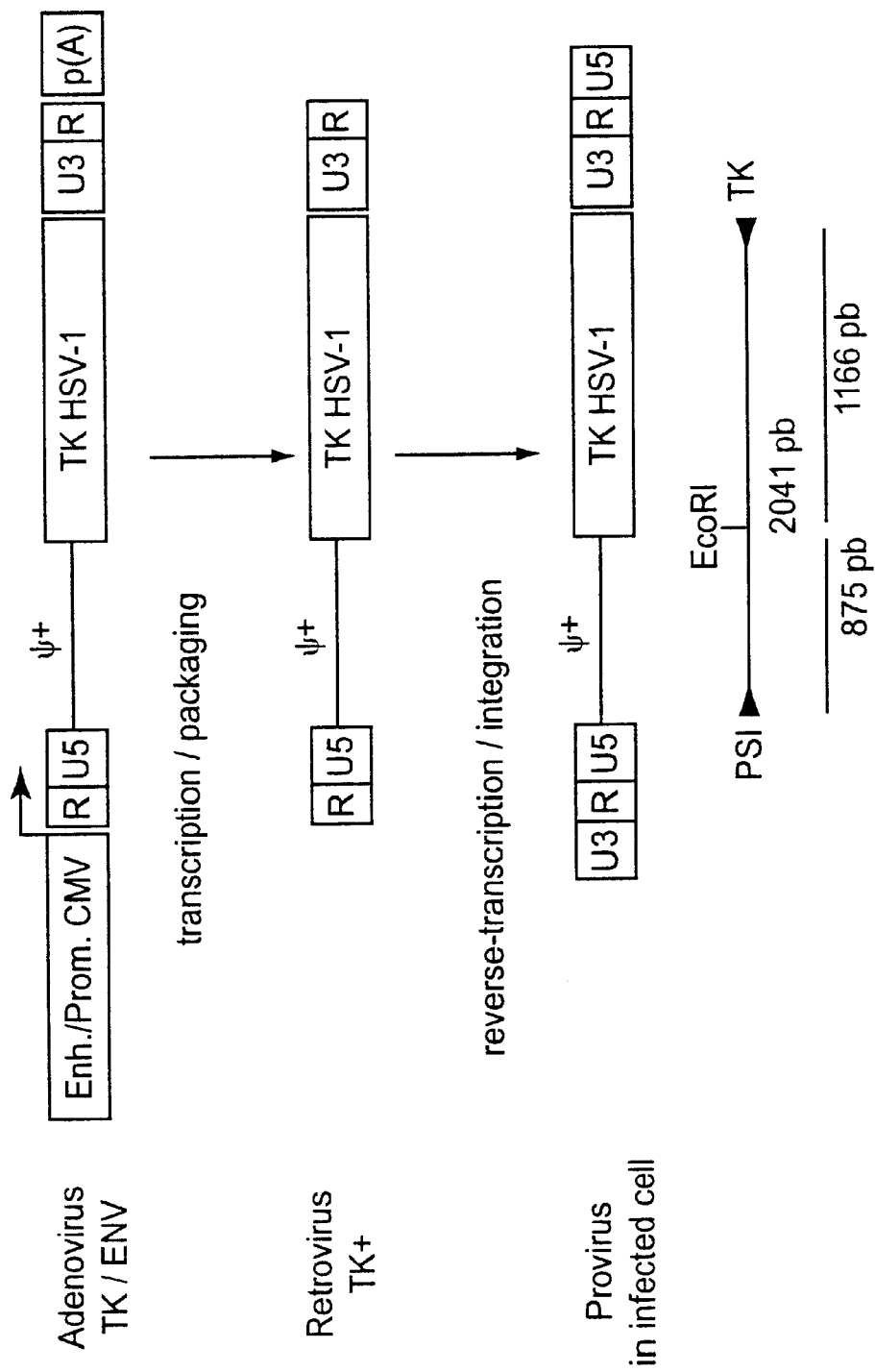

FIG. 10: Method of detection, by PCR and enzymatic cleavage, of the presence of an integrated or non-integrated retroviral TK cassette.

Figure 11:
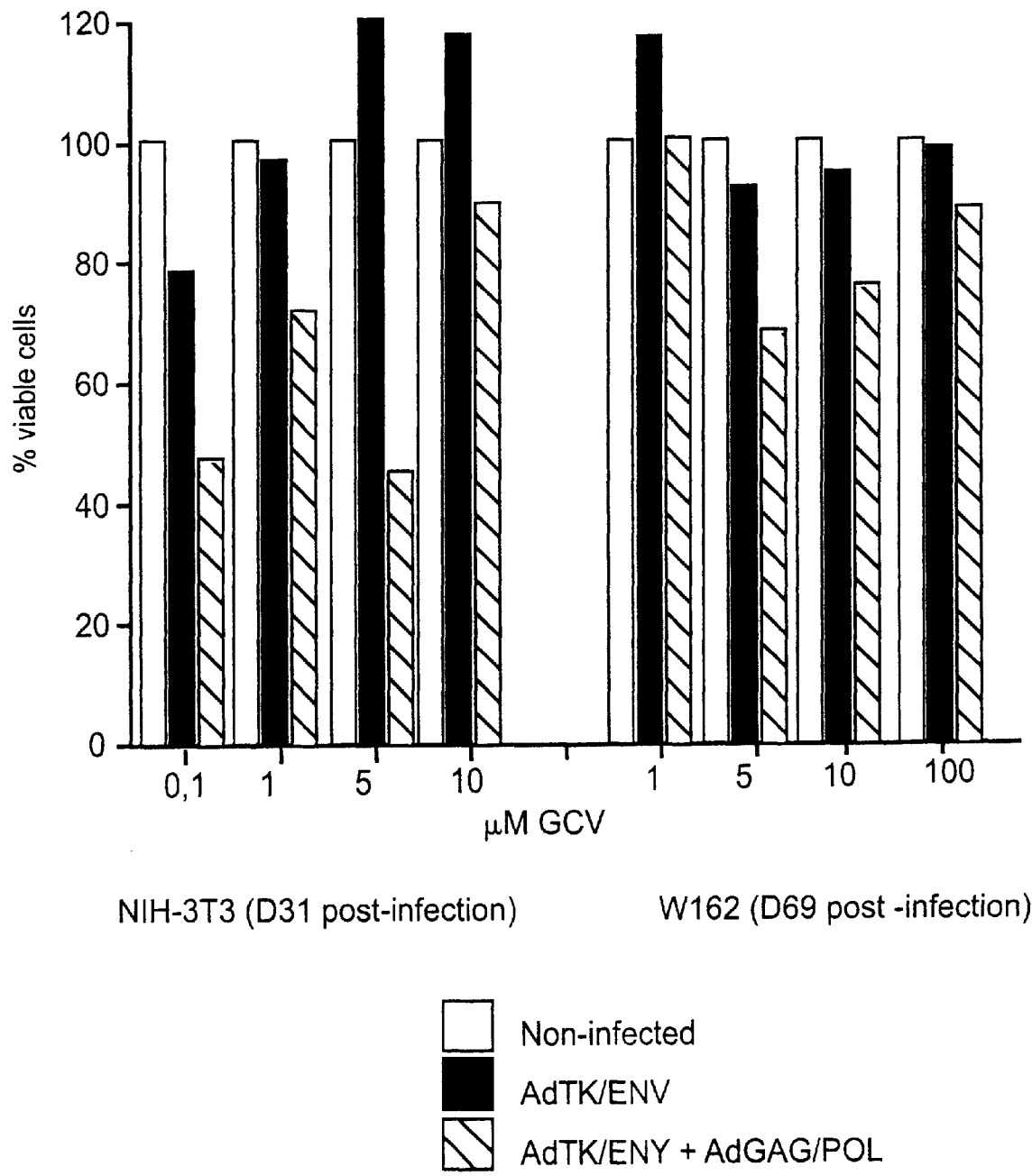

FIG. 11: Demonstration of gancyclovir sensitivity of cells infected by the TK retroviruses produced.

Figure 12A:
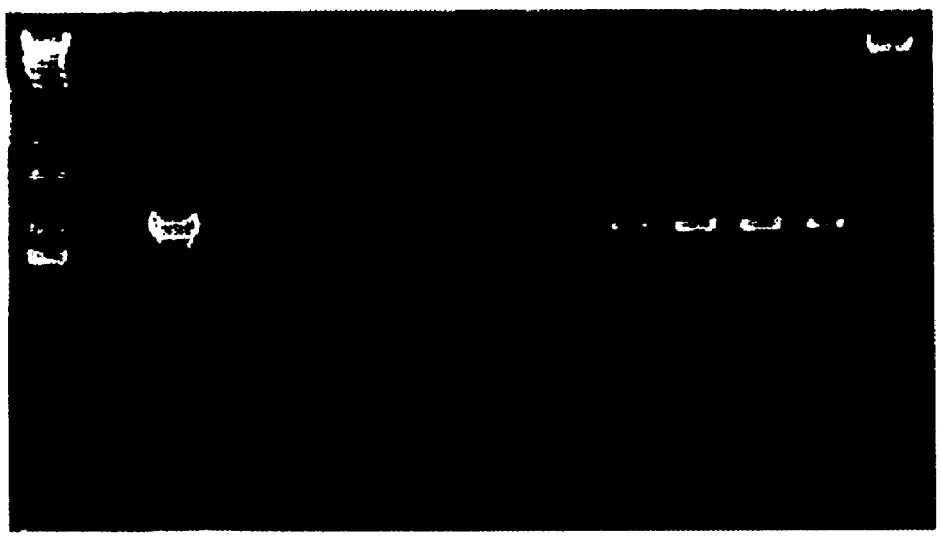
Figure 12B:
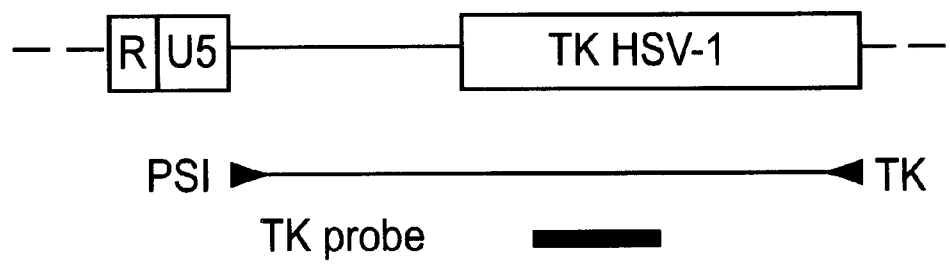
Figure 12B:
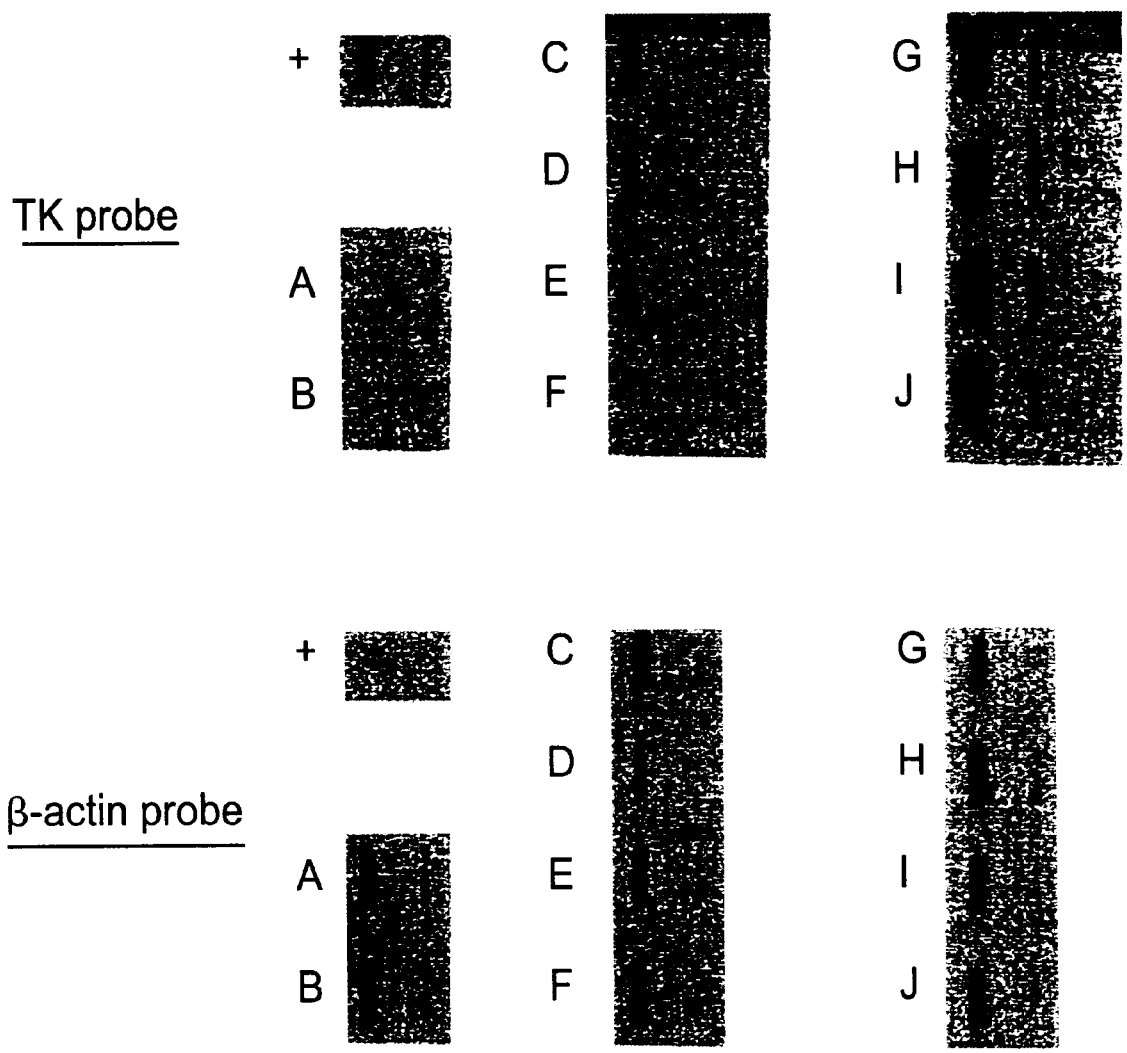

FIG. 12: Amplification of the TK gene in H460 tumor cells in vivo. Line M:1 kb marker (Gibco BRL); line–: no DNA; line+: pLTK plasmid.

Figure 13:

FIG. 13: Amplification of the TK provirus in H460 tumor cells in vivo.

GENERAL MOLECULAR BIOLOGY TECHNIQUES

The methods classically used in molecular biology, such as preparative plasmid DNA extraction, cesium chloride gradient centrifugation of plasmid DNA, agarose gel electrophoresis, purification of DNA fragments, phenol-chloroform protein extractions, DNA precipitation in saline medium by ethanol or isopropanol, transformation in *Escherichia coli*, etc . . . are well known to those skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, N.Y. 1987].

For ligation, the DNA fragments can be separated according to size by agarose gel electrophoresis, purified by the "QIAquick Gel Extraction Kit" distributed by Qiagen, then incubated in the presence of phage T4 DNA ligase (Biolabs) according to the supplier's recommendations. DNA 5' end dephosphorylation can be carried out with alkaline phosphatase (Boehringer Mannheim) according to the supplier's specifications. Protruding 5' end filling can be done with *E. coli* DNA polymerase I Klenow fragment (Biolabs) according to the manufacturer's instructions.

In vitro site-directed mutagenesis using synthetic oligonucleotides can be carried out according to the method developed by Mikaelian and Sergeant (Nucleic Acids Research, 1992, 20: 376). Amplification of DNA fragments by the so-called PCR technique (Polymerase-catalysed Chain Reaction, Saiki R. K. et al., 1985, Science 230: 1350–13541 can be accomplished by using Pfu DNA polymerase (Stratagene) according to the manufacturer's instructions. Nucleotide sequences can be checked by the method described by Sanger et al. (Proc. Nati. Acad. Sci. USA, 1977, 74: 5463–5467).

IGRP2 and W162 cells [Weinberg et al., PNAS (1983) 80: 5383] are grown in minimum Eagle's medium (MEM) supplemented with 10% fetal calf serum (FCS). Human (ATTC-HTB 177) non-small-cell lung cancer cells NCI-H460 and murine NIH-3T3 fibroblasts are grown in Dulbecco's modified medium and RMPI 1640, respectively, supplemented with 10% FCS. All cells are cultured at 37° C. in a 5% $CO_2$ atmosphere.

EXAMPLE 1

Construction of Three Plasmids Carrying Different Retroviral Units Under Control of a Promoter This example describes the construction of three plasmids, respectively containing expression cassettes for (i) the retroviral envelope 4070A, (ii) MoMLV gag-pol proteins and (iii) the HSV-1 tk gene in a retroviral background.

1.1. Construction of Ptasmid PEF1a-Env

The Hind3/Xba1 fragment containing the promoterlenhancer of the EF-1a gene from plasmid pEF-BOS (Mizushima and Nagata, 1990, Nuci. Acids Res. 18: 5322) is cloned into the Hind3 and Xba1 sites of commercially available plasmid pSI (Promega) to generate plasmid pSI-EF1a.

An Xba1/Not1 fragment containing the amphotropic MLV viral envelope gene 4070A (env 4070A) is amplified by PCR using plasmid pSV-envAM (gift of T. Heidmann, CNRS URA 147) as template and oligonucleotides SEQ ID No.1 and SEQ ID No. 2 descdbed below.

SEQ ID No. 1
   5'-GGCTCTAGAGCCGCCACCATGGCGCGTTC AACGCTC-3'

The Xba1 is in italics and the Kozak translation initiation consensus sequence is in bold type.

SEQ ID No. 2
   5'-GCGGCCGCTTATCATGGCTCGTACTCTATGG-3'

The Not1 site is in italics and the two stop codons are in bold type.

During this amplification, an intermediate PCR reaction using oligonucleotides SEQ ID No. 3 and SEQ ID No. 4 allows elimination of the Pac1 site present in the env gene without altering the amino acid sequence.

SEQ ID No. 3
   5'-CAGGCATGGAGTCAAAACCAGAGCCTGGAC-3'
SEQ ID No. 4
   5'-CACTGCCTTAATCAAAACCCAGCAG-3'

The altered Pac1 site is in bold type.

Figure 2B:
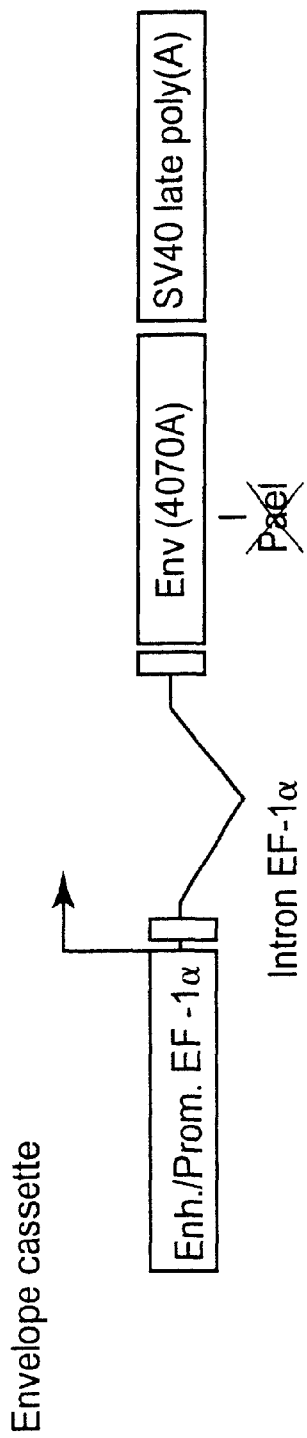

The amplified Xba1/Not1 fragment, containing the env 4070A gene, is cloned into the Xba1 and Not1 sites of pSi-EF1a to give plasmid pEF1a-Env which therefore contains the env4070A gene under control of the EF-1a promoter and followed by the SV40 virus late polyadenylation signal. The Env cassette in this plasmid is depicted in FIG. 2B.

1.2. Construction of Plasmid pEF1a-GP+CNRS URA 147) containing the gag cistron and a part of the pol cistron of the Moloney strain MLV virus is cloned into the Xma1 site of pSI-EF1 a (see §1.1.) to produce plasmid pEF1a-GP.

An EcoR1/BsrG1 fragment containing the 5' end of the gag cistron is amplified by PCR using plasmid pMOV-3ACla as template with oligonucleotides SEQ ID No. 5 and SEQ ID No. 6 described below.

SEQ ID No. 5
   5'-CCGGAATTCGCCGCCACCATGGGCCAGAC TGTTACC-3'

The EcoR1 site is in italics and the Kozak translation initiation consensus sequence is in bold type.

SEQ ID No. 6
   5'-GGAGGCGGAGGCTTAGGGTG-3'.

The amplified EcoR1/BsrG1 fragment is cloned into the EcoR1 and BsrG1 sites of pEF1a-GP to produce plasmid pEF1a-GPaug.

An Xma1/Not1 fragment containing the 3' end of the pol cistron is amplified by PCR using plasmid pMOV-3ΔCla as template with oligonucleotides SEQ ID No. 7 and SEQ ID No. 8 described below.

SEQ ID No. 7
   5'-GTAGACGGCATCGCAGCTTG-3'
SEQ ID No. 8
   5'-AAAAAAAAGCGGCCGCTCATTAGGGGCC TCGCGGG-3'

The Not1 site is in italics and the stop codons are in bold.

Figure 2C:
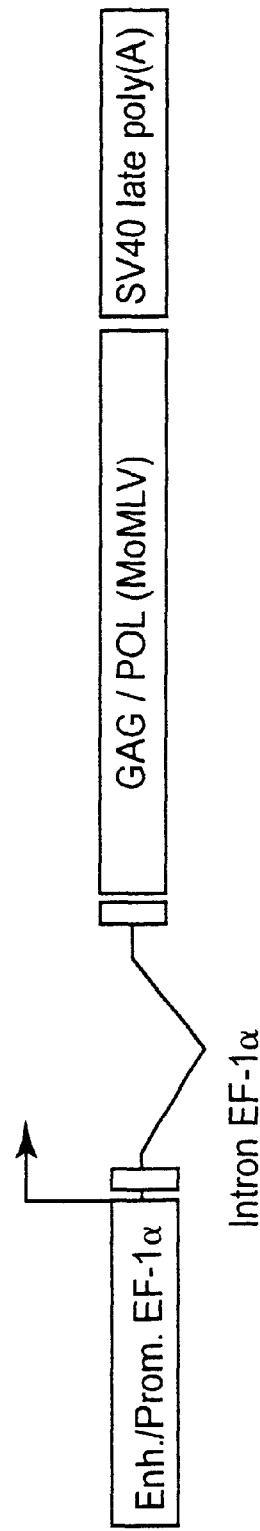

The amplified Xma1/Not1 fragment is cloned into the Xma1 and Not1 sites of pEF1a-GPaug to give plasmid pEF1a-GP+ which therefore contains the gag-pol cistron under control of the EF-1a promoter and followed by the SV40 virus late polyadenylation signal. The GAG/POL cassette in this plasmid is depicted in FIG. 2C.

1.3. Construction of Plasmid pCLTKRpA

The BstY1/Nar1 fragment of pXL3022, containing the HSV-1 tk gene and its leader sequence, is cloned into the Bcl1 and Cla1 sites (compatible sites) of the retroviral vector pLNCX (Miller and Rosman, 1989, Biotechniques 7:980–990) to generate pLTK.

The Sac1/Sac1 and Sac1/Nhe1 fragments of pLTK are cloned in the Sac1 and Nhe1 sites of the commercially available plasmid pCI (Promega), containing the hCMV-IE (−733/−14) promoter/enhancer, to produce pCLTK.

An Nhe1/Not1 containing three-quarters of the U3 sequence and the R sequence, is amplified by PCR using plasmid pLNCX as template with oligonucleotides SEQ ID No. 9 and SEQ ID No. 10 described below.

SEQ ID No. 9
   5'-GACCCCACCTGTAGGTTTGGC-3'
SEQ ID No. 10
   5'-AAAAAAAAGCGGCCGCTGCAACTGCAAG AGGG-3'

The Not1 site is in italics. The amplified Nhe1/Not1 fragment is cloned into the Nhe1 and Not1 sites of pCLTK to produce pCLTKR.

A Not1/BamH1 fragment containing the polyadenylation signal of the bgh (bovine growth hormone) gene is amplified by PCR using the commercially available plasmid pcDNA3 (Invitrogen) as template with oligonucleotides SEQ ID No. 11 and SEQ ID No. 12 described below.

SEQ ID No. 11

5'-AAAAAAAAGCGGCCGCTAAATGCTAGAGC TCGCTG-3'

The Not1 site is in italics.

SEQ ID No. 12

5'-CGCGGATCCCCACCGCATCCCCAGC-3'

The BamH1 site is in italics.

The amplified Not1/BamH1 fragment is cloned into the Not1 and BamH1 sites of pCLTKR to generate pCLTKRpA which therefore contains the tk gene in a retroviral vector background. In the 5' LTR, the U3 sequence is replaced by the hCMV/IE promoter/enhancer. It has been reported that this hybrid LTR (hCMV-R-U5) is functional (Naviaux et al., 1996, J. Virol. 70:5701–5705). In the 3' LTR, the U5 sequence has been deleted and replaced by the bgh gene polyadenylation signal. The structure of the cassette obtained is given in FIG. 2A.

EXAMPLE 2

Construction of two "Shuttle" Plasmids Carrying Different Retroviral Units in View of E. coli Technology This example describes the construction of two so-called "shuttle" plasmids which will be used to construct two recombinant adenoviruses by means of E. coli technology (see example 3). They contain the expression cassettes Tk and Env (pAdCLTKEE), and Gag-Pol (pAdEGP). (FIG. 3)

2.1. Construction of "Shuttle" Plasmid pAdEGP (FIG. 3)

The Fsp1/Fsp1 fragment of pEF1a-GP+, containing the gag-pol cistron under control of the EF-1a promoter (see §1.2.), is cloned in the dephosphorylated EcoRV site of pXL3048 (plasmid carrying Kana and SacB selection genes) to generate plasmid pAdEGP which thus contains sequences 1–382 and 344–64296 of adenovirus type 5 respectively located 5' and 3' of the Gag-Pol expression cassette.

2.2. Construction of "Shuttle" Plasmid 1pAdCLTKEE (FIG. 4)

The Bgl2/BamH1 fragment of pCLTKRpA containing the TK cassette in a retroviral background (see §1.3.) is cloned into the BamH1 site of pXL3048 (plasmid carrying Kana and SacB selection genes; RPR-Gencell) to generate plasmid pAdCLTK.

The Avr2/Ear1 (Kienow-treated) fragment of pEF1a-Env containing the Env expression cassette (see §1.1.) is cloned into the Sal1 site (treated with alkaline phosphatase then Klenow fragment) of pAdCLTK to generate plasmid pAdCLTKEE which thus contains sequences 1–382 and 344–64296 of adenovirus type 5 respectively located 5' and 3' of the TK-env expression cassette. The Env4070A expression cassette, located 3' of the TK expression cassette, is transcribed in the opposite direction.

EXAMPLE 3

Construction of Two E1⁻/E3⁻/E4⁻Recombinant Adenoviral Vectors Carrying Different Retroviral Units This example describes the construction of two E⁻1/E3⁻/E4⁻recombinant adenoviral vectors respectively containing TK-Env (AdTK/ENV) and Gag-Pol (AdGAG/POL) expression cassettes by means of double recombination in E. coli.

3.1. E. coli Technology

E. coli technology enables the construction of an infectious recombinant adenoviral genome from a modified adenovirus 5 genome and a "shuttle" plasmid (carrying the cassette to be integrated in the adenoviral genome), after two successive homologous recombinations in an E. coli polA mutant strain. The method has been amply described by Crouzet et al. (1997, Proc. Natl. Acad. Sci. USA 94: 1414–1419).

3.2. Construction of Recombinant Genomes AdGAG/POL and AdTK/ENV

The adenoviral type 5 genome, used for E. coli technology, is cloned into plasmid pXL2811 (Crouzet et al., supra). This genome, carried on a Pacd fragment, bears deletions in the regions E1 (ΔE1: Hinf1-Bgl2 deletion 382–3328), E3 (ΔE3: Xba1 deletion 28592–30470) and E4 (ΔE4: Ssp1-Sma1 deletion 33423–35356).

The AdGAG/POL recombinant adenoviral genome is constructed after homologous recombinations in E. coli between the "shuttle" plasmid pAdEGP (see §2.1) and pXL2811. The Gag-Pol expression cassette is located in the E1 deletion.

The AdTK/ENV recombinant adenoviral genome is constructed after homologous recombinations in E. coli between the "shuttle" plasmid pAdCLTKEE (see §2.2.) and pXL2811. The TK-env expression cassette is located in the E1 deletion.

The two recombinant DNA preparations are analyzed by enzymatic digestion followed by electrophoresis on a 0.7% agarose gel. They are also sequenced (cloning sites. sequences amplified by PCR . . . ). The restriction enzymes are chosen in particular to verify that the TK, Env and Gag-Pol expression cassettes remain intact in their adenoviral background.

The number and size of the bands obtained and the sequenced regions are fully consistent with the expected profiles. No deletions or mutations are observed in the two genomes. These results indicate on the one hand that the two adenovirus genome constructs are correct and on the other hand that the integrated retroviral sequences, including modified LTRs, do not generate internal recombination during construction in E. coli, thereby ensuring genetic stability of the adenoviral DNA.

EXAMPLE 4

Production and Characterization of the AdGAG/POL and AdTK/ENV Viral Prestocks

This example describes the production, characterization and titration of the two recombinant adenoviruses, AdTK/ENV and AdGAG/POL.

4.1. Production of AdTK/ENV and AdGAG/POL Adenoviruses

The AdTK/ENV and AdGAG/POL DNAs (20 μg) are digested by Pacd to release the Pac1 fragment containing only the recombinant adenoviral genome, then precipitated in ethanol. Each of the two DNAs is transfected with LipofectAMINE (GibcoBRL), according to the supplier's instructions, into cell line 293 trans-complementing for adenoviral proteins E1 and E4 (IGRP2 cells; Yeh et al., 1996, J. Virol. 70: 559–565).

Cells are maintained in culture until onset of a cytopathic effect (cell detachment). At this time, the supernatant is removed and freeze-thawed three times before being used to infect new IGRP2 cells. Thus, the two recombinant adenoviruses are successively amplified in 12 well culture plates (ampli. 1), 6 well culture plates (ampli. 2) and 10 cm culture dishes (ampli. 3 and 4). For each virus, the final prestock of approximately 150 ml is taken from 35 10-cm dishes (ampli. 4). It is also freeze-thawed three times, then stored at −20° C.

4.2. Characterization of the Genetic Stability of the AdTK/ENV and AdGAG/POL Viruses This is designed to verify the integrity of the AdTK/ENV and AdGAG/POL adenoviral genomes following amplification of the viruses in cell culture.

A 2 ml aliquot of each prestock is used to purify viral DNA according to the method described by Gluzman and Van Doren (1983, J. Virol. 45: 91–103). The purified DNA is analyzed by enzymatic digestion followed by electrophoresis on a 0.7% agarose gel. The choice of restriction enzymes makes it possible in particular to check the integrity of the three expression cassettes TK, Env and Gag-Pol in their adenoviral background.

The number and size of the bands obtained fully correspond to the predicted profiles. No deletions are observed in the two genomes. These results indicate that the retroviral sequences integrated in the two adenoviral genomes do not alter the stability of these genomes.

4.3. Titration of AdTK/ENV and AdGAG/POL Viral Prestocks

The two viral prestocks obtained were titrated by two methods: (i) immunotitration with anti-penton monoclonal antibody and (ii) High-Pressure Liquid Chomatography or HPLC (F. Blanche, RPR-Gencell), in particular in order to estimate the productivity of each virus.

For immunotitration, IGRP2 cells grown in 6 well plates are infected with dilutions of viral prestock. 48 hours post-infection, cells are fixed in 90% methanol then incubated for 1 hour in PBS/5% FCS (fetal calf serum) for saturation. Cells are then incubated with anti-penton monoclonal antibody (Biodesign International) at 1:100 dilution, washed, then labeled with peroxidase-conjugated antibody at 1:500 dilution (Amersham). Labeled cells are revealed by 3,3'-diaminobenzidine (DAB)/$H_2O_2$.

As determined by immunotitration, the number of infectious particles (IP) is $5.8 \times 10^8$ IP/ml for AdTK/ENV and $3.3 \times 10^8$ IP/ml for AdGAG/POL. As determined by HPLC, the number of viral particles (VP) is $1.9 \times 10^{10}$ VP,ml for AdTKlENV and $1.3 \times 10^{10}$ VP/ml for AdGAG/POL. The VP/IP ratio is 33 (AdTK/ENV) and 39 (AdGAG/POL).

The viral titers so obtained demonstrate good productivity of the two prestocks, AdGAG/POL and AdTK/ENV. This level of productivity is similar to that of other E1 and E4-defective recombinant adenoviruses. These data suggest, in particular, that the presence of retroviral sequences and of their functions does not interfere with the adenoviral sequences and their functions in terms of viral productivity.

EXAMPLE 5

Functionality of the Retroviral Expression Cassettes in AdTK/ENV and AdGAG/POL Adenoviruses This example describes the study of functionality of the TK expression cassette in adenovirus AdTK/ENV and the Gag-Pol expression cassette in AdGAG/POL. Functionality of the Env expression cassette is tested by titrating the recombinant retroviruses produced (see §6.4.).

5.1. Functionality of TK Expression Cassette

Functionality of the expression cassette is analyzed in three ways: (i) quantification of TK+ RNA, (ii) demonstration of TK protein in cell lysate, and (iii) fluorescent labeling of cells expressing TK protein. Cells infected with AdGAG/POL and with a recombinant adenovirus expressing the tk gene served as negative control and positive control, respectively, in each experiment.

48 hours post-infection of W162 cells (cells derived from Vero cells, originating from green monkey kidney) with AdTK/ENV (MOI 10 to 837 IP), total RNAs are extracted with the RNeasy kit (Qiagen) according to the supplier's instructions. RNAs (15 µg) are deposited on a nylon membrane, then hybridized with a radiolabeled TK probe according to the protocols described in Maniatis T. et al. ("Molecular Cloning, a Laboratory Manual", Cold Spring Harbor Laboratory, Cold Spring Harbor, N.Y., 1982). This analysis allows specific quantification of TK+ RNA.

AdTK/ENV-infected W162 cells are harvested 48 hours post-infection, then lysed to detect the presence of TK protein by ELISA.

AdTK/ENV-infected W162 cells (MOI 50 to 200 IP) are harvested 48 hours post-infection, fixed in 4% formaldehyde for 30 minutes, then lysed in 0.2% Triton for 10 minutes. Cells are then incubated with anti-TK rabbit IgG antibody (pAbTK41, RPR-Gencell) at 1:250 dilution, washed in Power-Block buffer 1×(Biogenex), then labeled with FITC-conjugated rabbit anti-lgG antibody at 1:250 dilution (Jackson ImmunoResearch Laboratories). Labeled cells are analyzed by flow cytometry (FACS).

The results indicate that the TK+ RNAs are transcribed. The amount of transcribed TK+ RNA is proportional to the MOI of AdTK/ENV adenovirus infection. The TK protein is detected in the lysate of infected cells and 70% to 90% of infected cells (according to MOI) are positively labeled.

Together, these data clearly show that the TK expression cassette is functional on both the transcriptional and translational levels.

5.2. Functionality of Gag/Pol Expression Cassette

Functionality of the expression cassette is studied by testing for the presence of reverse transcriptase activity, encoded by the pot cistron, in AdGAG/POL-infected W162 cell supernatants. In the culture supematant, the enzyme reverse transcriptase (RT) is present in the retroviral particle whose components are encoded by the gag cistron. The presence of reverse transcriptase activity therefore demonstrates that retroviral particles are present, i.e. that gag proteins are present. Supematants of AdTK/ENV-infected W162 cells and of GP+envAM12 cells [retroviral particle-producing murine cell line; (Markowitz et al., 1988, Virology 167: 400–406)] served as negative control and positive control, respectively.

An aliquot of 30 µl of supernatant from AdGAG/POL-infected W162 cells (MOI 10 to 500 PI) is taken 48, 72 and 96 hours post-infection and used in a reverse transcriptase test (RT test) according to the protocol described by Goff et al. (1981, J. Virol. 38: 239–248).

The RT test demonstrates the presence of reverse transcriptase activity, therefore of retroviral particles, in the supernatant of cells infected by AdGAG/POL. Retroviral particle production is maximum for an MOI of about 200 PI (results of two independent tests).

These data clearly show that the Gag/Pol expression cassette is functional.

EXAMPLE 6

Production of Recombinant Retroviral Particles in Vitro After Colinfection with AdTK/ENV-AdGAG/POL Adenoviruses This example describes the use of cells simultaneously infected (co-infected) with AdTK/ENV and AdGAG/POL for the production of infectious recombinant retroviral particles in vitro. The general outline of viral particle production is given in FIG. 5.

6.1. Coinfection with AdTK/ENV-AdGAG/POL Adenoviruses

This consisted in comparing reverse transcriptase activity, i.e., viral to productivity, in supernatants of W162 cells coinfected with AdGAG/POL and AdTK/ENV (MOI 5/5 PI) and W162 cells infected with AdGAG/POL alone (MOI 5 PI). Supernatants from W162 cells infected with AdTKIENV and from GP+envAM 12 cells served as negative control and positive control, respectively.

An aliquot (30 µl) of each supernatant is taken 48, 72 and 96 hours post-infection and used for an RT test.

There are no differences over time between coinfected cells and cells infected with AdGAG/POL alone, demonstrating that there is no interference between Gag-Pol and Env retroviral functions on the one hand, and between adenoviral and retroviral functions on the other hand.

6.2. Time Course of Retroviral Particle Production

The time course of production of retroviral particles is studied after co-infecting W162 cells with AdTK/ENV and AdGAG/POL (MOI 5/5 PI).

A 30 µl aliquot of supernatant is taken at regular intervals for 15 days post-infection and used for an RT test. The culture medium is replaced 24 hours before each sampling. Infected cells are maintained in culture for 15 days without passaging.

The results are given in FIG. 6. They show that retroviral particle production increases very rapidly between days 0 and 4 and then gradually decreases between days 5 and 15. During the first 7 days, viral production levels range between 50 and 100%. The development of several layers of cells after 1 week of culture may lead to an underestimation of viral productivity, since viruses transmitted from cell to cell by membrane fusion, without being released into the supernatant, are not detected in the RT test.

FIG. 7 and Table 1 give the level of retroviral particle production in W162 cells according to MOI of infection with adenoviruses AdTK/ENV and AdGAG/POL. As shown in Table 1, the activity of coinfected W162 cells is roughly proportional to the MOI used, up to 200 IP/cell. At higher MOI,(300 and 350 IP/cell), there is no further increase in RT activity. An MOI of 200 therefore appears to be optimal for production of retroviral particles. In this respect, the results show that RT activity measured in the system of the invention is up to 30 times higher than that measured in the same conditions in the supernatant of GP +envAm12 packaging cells, confirming the advantageous aspects of the present invention for the production of retroviral particles (Table 1). Furthermore, the high RT activity persists beyond one week in coinfected cells, as opposed to the methods of the prior art where RT activity decreases after 48 to 96 hours (Vile et al., Br. Med. Bull. 51 (1995) 12], further demonstrating the advantageous features of the present invention.

6.3. Packaging of TK RNA into Retroviral Particles

The aim is to detect and quantify TK+ RNAs packaged in viral particles roduced after coinfecting W162 cells with AdGAG/POL and AdTK/ENV at ifferent MOI.

Cell supernatants are taken 72 hours post-infection and RNA is extracted from retroviral particles according to the method of Murdoch et al. (1997, Gene Ther. 4: 744–749). RNAs are deposited on a nylon membrane, then hybridized with a radiolabeled TK probe according to the protocols described by Maniatis T. et al. ("Molecular Cloning, a Laboratory Manual", Cold Spring Harbor Laboratory, Cold Spring Harbor, N.Y., 1982).

The results obtained are presented in FIG. 8 and demonstrate the presence of TK+ RNA in the resultant viral particles. The amount of packaged TK+ RNA is proportional to the MCI of the adenoviral coinfection.

The presence of TK+ RNA in the retroviral particles indicates that the packaging mechanism is functional and that the viral particles can transmit the recombinant genome in the infected cells.

6.4. Titration of Infectious Recombinant Retroviral Particles

The aim is to estimate the quantity of infectious retroviral particles produced after coinfecting W162 cells with AdGAG/POL and AdTK/ENV.

Supernatants of coinfected cells are taken 48 hours post-infection. Dilutions of supernatant are deposited on NIH-3T3 cells (NIH mouse tail fibroblasts). NIH-3T3 TK+ cells are counted by flow cytometry (FACS) 48 hours post-infection. Cells are harvested and fixed in 4% formaldehyde for 30 minutes, then lysed in 0.2% Triton for 10 minutes. Cells are incubated with anti-TK rabbit IgG antibody (pAbTK41) at 1:250 dilution, washed in Power-Block buffer 1X (Biogenex), then labeled with biotin-conjugated rabbit anti-lgG antibody at 1:250 dilution (Sigma). After washing, cells are incubated for 1 hour with streptavidine-FITC at 1:500 dilution (Amersham) and analyzed by flow cytometry.

The mean retroviral titer on NIH-3T3 cells is $1.3 \times 10^5$ IU (infectious units)/ml. This indicates that the recombinant retroviruses produced are functional, i.e. infectious and able to transmit the TK expression cassette to the target cells. The calculated viral titer demonstrates that the productivity of infectious retroviral particles is equivalent to that of currently available packaging cell lines.

EXAMPLE 7

Presence and Long-term Expression of the tk Trangene In Vitro

This example is designed to demonstrate the presence and long-term expression of the TK retroviral cassette in cultures of cells coinfected with AdTKIENV and AdGAG/POL. Non-infected cells and AdTK/ENV-infected cells served as controls. Two cell types were infected : W162 and NIH-3T3.

7.1. Presence of a TK Retroviral Cassette Integrated in the Genome of Cells Infected In Vitro This involved testing for the presence of the TK retroviral cassette in the genome of cells cultured after coinfection with AdTKIENV and AdGAG/POL. Recall that the gag-pol cistron codes notably for the reverse transcriptase (RT) and integrase (IN) proteins required for reverse transcription and integration of the retroviral genome in the infected cells.

Genomic DNA of the cultured cells is extracted (NIH-3T3: D17 and D50 p.i.; W162: D52 and D94 p.i.), then purified with the "QIAamp tissue kit" (Qiagen) according to the supplier's instructions. DNA (2 µg) is used as template in a PCR reaction with oligonucleotide SEQ ID No. 13, corresponding to the sequence complementary to the 5' end of the U3 region, and oligonucleotide SEQ ID No. 14, corresponding to the sequence complementary to the 3' end of the tk gene, described below.

SEQ ID No. 13
    5'-GCTAGCTTMGTAACGCCATTTTGC-3'
SEQ ID No. 14
    5'-GCGCCAGGTCGCATATCGTCGG-3'

These oligonucleotides were chosen so as to amplify a 2610 nt fragment which can be cleaved (EcoRl site) into two fragments of 1444 nt and 1166 nt (see FIG. 9). This fragment is visualized by 0.7% agarose gel electrophoresis.

At all time points, a PCR fragment with the expected profile (size +EcoR1 digestion) is present in the NIH-3T3 and W162 cells coinfected with AdTK/ENV and AdGAG/POL. It was checked that this fragment specifically hybridizes with a tk-complementary probe (Southern blot analysis). Note that in our experiment, the signal is stronger in NIH-3T3 cells. No fragments are detected in the cultures of non-infected cells or cells infected with AdTK/ENV alone.

These data indicate that the TK expression cassette was transmitted, via the recombinant retroviruses produced, to cells grown in the presence of cells coinfected with AdTK/ENV and AdGAG/POL. The late time points used in the test and the absence of signals in the control cultures confirm that the TK cassette is integrated in the cellular genome. Furthermore, the presence of the 5' U3 sequence, characterized by the possibility of amplifying the PCR fragment, indicates that the reverse transcription process is complete.

Coinfection of cells with the adenoviral-retroviral chimeric vectors AdTK/ENV and AdGAG/POL, in contrast to infection with AdTK/ENV alone, therefore allows integration of the TK expression cassette, a necessary step for long-term expression of the protein.

These results were confirmed by using the oligonucleotide pair SEQ ID NO: 15 5'-GCTCGTCCGGGATTTGGAGACCC-3' (sequence complementary to 5' end of packaging sequence) and SEQ 14 (FIG. 10).

7.2. Assessment of Gancyclovir (GCV) Toxicity on Cells Infected in Culture

This is a test for the presence of functional TK protein in cells cultured after coinfection with AdTK/ENV and AdGAG/POL. To this end, cells are incubated in the presence of gancyclovir (GCV). Recall that HSV-1 thymidine kinase converts nucleoside analogs, such as gancyclovir or acyclovir, to toxic drugs that arrest cell division by inhibiting DNA synthesis.

NIH-3T3 cells (D31 p.i.) and W162 cells (D69 p.i.) are incubated in the presence of gancyclovir (Roche) at a suitable concentration range (NIH-3T3: 0.1, 1, 5 and 10 $\mu$M; W162: 1, 5, 10 and 100 $\mu$M) for 3 to 5 days. Viable cells are counted with the kit "CellTiter AQueous One Solution Cell Proliferation assay" (Promega) according to the supplier's instructions.

The results obtained are presented in FIG. 11. Gancyclovir sensitivity is observed in cell cultures coinfected with AdTK/ENV and AdGAG/POL. An average of 40% (NIH-3T3) to 18% (W162) of cells are sensitive to GCV. This difference in sensitivity between the two cell types may be related to the amount of TK+ DNA fragment amplified by PCR, which is higher in the case of NIH-3T3 cells (see §7.2). Note that the number of gancyclovir-sensitive cells may be increased by a bystander effect (Fick, J. et al., 1995, Proc. Natl. Acad. Sci. USA. 92: 11071–11075).

These data demonstrate that the TK retroviral cassette integrated in the genome of cells cultured after coinfection with AdTK/ENV and AdGAG/POL, codes for a functional TK protein. Coinfection of cells with adenoviral-retroviral chimeric vectors AdTK/ENV and AdGAG/POL therefore allows longer-term expression of TK protein than infection of cells with AdTK/ENV alone.

EXAMPLE 8

Transaene Amplification In Vivo

The efficiency of the compositions of the invention for producing retroviruses and transferring nucleic acids was confirmed in vivo in tumor cells.

To this end, the human carcinoma cell line NCI-H460 was coinfected in vitro with adenoviruses AdTK/ENV and AdGAG/POL (MOI 100 IP/cell for each virus), or with adenovirus AdTK/ENV alone (MOI 100 IP/cell). Flow cytometric analysis showed that these conditions of infection give approximately 25% TK-positive cells. 20 hours post-infection, 5×10$^6$ cells were implanted subcutaneously in the flank of 4 to 6-week-old athymic nude mice (n=4). Animals were scarified 23 days post-infection and tumors were excised and analyzed for transgene presence and persistence. Non-infected cells were also implanted as control (n=2).

The presence (and amplification) of the transgene was demonstrated by PSI/TK PCR analysis of the tumors. To this end, total DNA was purified from 50 $\mu$g of tumor using the QIAamp blood kit (Qiagen). PCR was performed on 2 $\mu$g of total DNA using oligonucleotides TK (SEQ ID No. 14) and PSI with the sequence 5'-GCTCGTCCGGGATTTGGAGACCC-3' (SEQ ID No. 16) as primers, to generate a 2041 bp fragment from TK provirus and AdTKJENV DNA. Amplification was carried out for 35 cycles at a denaturing temperature of 95° C. for 45 seconds, an annealing temperature of 65° C. for 45 seconds, and an elongation temperature of 72° C. for 4 minutes 30 seconds. As control, PCR was performed on each DNA sample using the human O-Actin Control Amplimer (Clontech). The PCR products were revealed on 1% agarose gels by ethidium bromide staining.

The results are given in FIG. 12A and show that the tumors that develop after coinfection with adenoviruses AdTK/ENV and AdGAG/POL (tumors G, H, I and J) contain more copies of the TK gene than those which received only AdTK/ENV (tumors C, D, E and F) or those which received no virus (tumors A and B).

The increased transgene copy number was confirmed by quantitative slot-blot analysis. Thus, 1 $\mu$l of each amplification product from the PSI/TK PCR and the $\beta$-Mactin PCR was heated to 95° C. in 0.4 M NaOH, 2.2 mM EDTA for 2 minutes and transferred to a hybond-N+ nylon membrane (Amersham Life Sciences). The DNA was fixed and the membranes prehybridized at 65° C. for 2 hours in 0.25 M NaH$_2$PO$_4$,0.25 M Na$_2$HPO$_4$, 7% SDS, followed by overnight hybridization in the same conditions. Membranes were then washed twice at 65° C. with 2 ×SSC, 0.1% SDS for 5 minutes; twice at 65° C. with 2 ×SSC, 0.1% SDS for 15 minutes; and twice at 65° C with 0.1 ×SSC, 0.1% SDS for 30 minutes. The probe was the HSV-1 TK gene randomly labeled with ($\alpha$-$^{32}$P)-dCTP. Membranes were analyzed on a Fujix Bas 1000 phosphorimager (Fuji Photo Film Co.). The results are presented in FIG. 12B, and show a 10 to 50-fold increase in the number of tumor cells containing the TK gene, in comparison to tumors infected with AdTK/ENV alone.

TK gene integration into coinfected tumor cells was confirmed by PCR analysis (FIG. 13, lines G–J), whereas TK provirus could not be detected in cells infected with AdTKIENV alone (FIG. 13, lines 1A–F).

These results therefore demonstrate (i) the efficiency of the invention in vivo, (ii) the amplification of the transgene by means of the system of the invention and (iii) the integration of the transgene in the target cell chromosome in vivo. Together, these results illustrate the advantageous aspects of the present invention for transferring nucleic acids into cells and producing infectious retroviral particles.

TABLE 1

| Cell Supernatants | MOI | RT Activity |
|---|---|---|
| Non-Infected | — | 1 |
| GP + envAm12 | — | $4.9 \times 10^2$ |
| AdTK/ENV | 200 | 1 |
| AdGAG/POL | 200 | $1.7 \times 10^5$ |
| AdGAG/POL + AdTK/ENV | 10/10 | $1.9 \times 10^4$ |
| AdGAG/POL + AdTK/ENV | 50/50 | $6.4 \times 10^4$ |
| AdGAG/POL + AdTK/ENV | 100/100 | $1.4 \times 10^5$ |
| AdGAG/POL + AdTK/ENV | 200/200 | $1.7 \times 10^5$ |
| AdGAG/POL + AdTK/ENV | 300/300 | $1.7 \times 10^5$ |
| AdGAG/POL + AdTK/ENV | 500/500 | $1.5 \times 10^5$ |

What is claimed is:

1. Composition comprising the whole set of genetic elements required for constituting a retroviral particle, incorporated in one or several recombinant adenoviruses defective for all or part of the E1 and E4 regions at least.

2. Composition according to claim 1, wherein the genetic elements comprise a retroviral vector and nucleic acids coding for retroviral complementation functions.

3. Composition according to claim 2, wherein the genetic elements comprise:

a nucleic acid coding for a retroviral gag protein, a nucleic acid coding for a retroviral pol protein, a nucleic acid coding for an envelope protein, and a nucleic acid comprising, between two LTR regions, a retroviral packaging sequence and a nucleic acid sequence of interest.

4. Composition according to claim 1, wherein said genetic elements are incorporated in a same recombinant adenovirus.

5. Composition according to claim 1, wherein said genetic elements are distributed into two recombinant adenoviruses.

6. Composition according to claim 5, wherein it comprises a first recombinant adenovirus comprising, incorporated in its genome, one or several nucleic acids coding for retroviral gag and pol proteins, and a second recombinant adenovirus comprising, incorporated in its genome, a nucleic acid coding for an envelope protein, and a nucleic acid comprising, between two LTR regions, a retroviral packaging sequence and a nucleic acid sequence of interest.

7. Composition according to claim 1, wherein said genetic elements are distributed into three recombinant adenoviruses.

8. Composition according to claim 3, wherein the gag and pol proteins are proteins from retroviruses chosen from among MoMLV, ALV, BLV, MMTV, and RSV.

9. Composition according to claim 3, wherein the envelope protein is a viral or cellular protein allowing retroviral particles to infect human cells.

10. Composition according to claim 9, wherein the envelope protein is an envelope protein from a GALV, A4070, RD114, VSV-G or rabies virus.

11. Composition according to claim 3, wherein the LTR region or regions are complete retroviral LTR regions or subdomains allowing reconstitution of complete LTRs after reverse transcription.

12. Composition according to claim 11, wherein the 5' LTR is deleted for the U3 domain and the 3' LTR is deleted for the U5 domain.

13. Composition according to claim 1 wherein the genetic elements allow the constitution of a lentivirus particle.

14. Composition according to claim 1, wherein the recombinant adenovirus or adenoviruses are defective for all or part of regions E1, E4 and E3.

15. Composition according to any claim 1, wherein the recombinant adenovirus or adenoviruses are defective for all or part of regions E1, E4 and E2.

16. Composition according to any claim 1, wherein the recombinant adenovirus or adenoviruses are defective for all or part of regions E1, E4 and E2 and E3.

17. Composition according to any claim 14, wherein the recombinant adenovirus or adenoviruses are further defective for all or part of the genes encoding the adenoviral late functions.

18. Composition according to any claim 1, wherein the recombinant adenovirus or adenoviruses are defective for any viral coding region.

19. Recombinant adenovirus defective for all or part of regions E1 and E4 at least, wherein it comprises, incorporated in its genome one or several nucleic acids coding for retroviral gag and pol proteins.

20. Defective recombinant adenovirus, wherein it comprises, incorporated in its genome, a nucleic acid coding for an envelope protein, and a nucleic acid comprising, between two complete or not LTR regions, a retroviral packaging sequence and a nucleic acid sequence of interest.

21. Composition comprising a recombinant adenovirus according to claim 19 and a recombinant adenovirus according to claim 20.

22. Cell modified by a composition according to claim 1 or 21 for the preparation of a product intended for transferring nucleic acids into cells in vivo.

23. Method for producing retroviral particles in vitro, comprising incubating cells in the presence of a composition according to claim 1.

24. Method according to claim 23, wherein the ceils are cells of human origin.

25. A composition comprising one or several E1, E4-defective recombinant adenoviruses wherein said one or several recombinant adenoviruses comprise, alone or in combination, nucleic acid sequences encoding, upon expression, a retroviral particle expressing a retroviral envelope and comprising a genome.

26. A composition comprising one or several E1, E4-defective recombinant adenoviruses, wherein said defective recombinant adenoviruses comprise a defective genome, said defective genome comprising nucleic acid sequences of a retroviral vector and of retroviral structural proteins.

* * * * *

SEQUENCE LISTING

<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
ggctctagag ccgccaccat ggcgcgttca acgctc                           36

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
aaaaaaaagc ggccgcttat catggctcgt actctatgg                        39

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
caggcatgga gtcaaaacca gagcctggac                                  30

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cactgcctta atcaaaaccc agcag                                       25

<210> SEQ ID NO 5
<211> LENGTH: 36
<212> TYPE: DNA

```
<213> ORGANISM: Artificial Sequence
<220> FEATURE:
<223> OTHER INFORMATION: Description of Artificial Sequence:
      Oligonucleotide

<400> SEQUENCE: 5
ccggaattcg ccgccaccat gggccagact gttacc                    36

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ggaggcggag gcttagggtg                                      20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gtagacggca tcgcagcttg                                      20

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
aaaaaaaagc ggccgctcat tagggggcct cgcggg                    36

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gaccccacct gtaggtttgg c                                    21

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
aaaaaaaagc ggccgctgca actgcaagag gg                        32

<210> SEQ ID NO 11
<211> LENGTH: 35
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 11
aaaaaaaagc ggccgctaaa tgctagagct cgctg                         35

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
cgcggatccc caccgcatcc ccagc                                    25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
gctagcttaa gtaacgccat tttgc                                    25

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
gcgccaggtc gcatatcgtc gg                                       22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
gctcgtccgg gatttggaga ccc                                      23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gctcgtccgg gatttggaga ccc                                      23
```